United States Patent [19]
Bis et al.

[11] Patent Number: 5,968,875
[45] Date of Patent: Oct. 19, 1999

[54] 2-METHOXYIMINO-2-(PYRIDINYLOXYMETHYL)PHENYL ACETAMIDES WITH CARBOXYLIC ACID DERIVATIVES ON THE PYRIDINE RING

[75] Inventors: Scott J. Bis, Midland, Mich.; Emily J. Canada; David H. Cooper, both of Indianapolis, Ind.; Christopher S. Galka; Neil Kirby, both of Carmel, Ind.; David G. Ouimette, Kuala Lumpur, Malaysia; David E. Podhorez, Midland, Mich.; Mary Pieczko, Indianapolis, Ind.; Rebecca Rezac, Carmel, Ind.; Brent J. Rieder, Greenfield, Ind.; John K. Swayze; Vidyadhar B. Hegde, both of Carmel, Ind.; Gary L. Sampson, Martinsville, Ind.

[73] Assignee: Dow AgroSciences LLC, Indianapolis, Ind.

[21] Appl. No.: 09/015,279

[22] Filed: Jan. 29, 1998

Related U.S. Application Data

[60] Provisional application No. 60/036,858, Feb. 3, 1997.

[51] Int. Cl.[6] .......... A01N 43/40; C07D 213/78; C07D 213/55
[52] U.S. Cl. .......... 504/244; 546/291; 546/322; 546/298

[58] Field of Search .......... 546/291, 322, 546/298; 504/244

[56] References Cited

U.S. PATENT DOCUMENTS

| | | | |
|---|---|---|---|
| 5,185,342 | 2/1993 | Hayase et al. | 514/274 |
| 5,371,222 | 12/1994 | Hayase et al. | 544/316 |
| 5,371,223 | 12/1994 | Hayase et al. | 544/316 |
| 5,401,877 | 3/1995 | Hayase et al. | 564/147 |
| 5,548,078 | 8/1996 | Hayase et al. | 544/298 |

OTHER PUBLICATIONS

Fortunak, et al; Preparation of Mappicine Ketones from Campthothecins: Chemistry of te Camptothecin E Ring; *Tetrahedron Letters*, vol. 35, No. 32, pp. 5763–5764, 1994.

*Primary Examiner*—Alan L. Rotman
*Attorney, Agent, or Firm*—Donald R. Stuart

[57] ABSTRACT

The present invention provides novel 2-methoximino-2-(pyridinyloxymethyl)phenyl acetamide compounds with carboxylic acid substituents on the pyridine ring, their use as fungicidal compounds, and their use in fungicidal compositions comprising at least one of the 2-methoximino-2-(pyridinyloxymethyl)phenyl acetamide compounds as the active ingredient.

16 Claims, No Drawings

2-METHOXYIMINO-2-(PYRIDINYLOXYMETHYL)PHENYL ACETAMIDES WITH CARBOXYLIC ACID DERIVATIVES ON THE PYRIDINE RING

RELATED APPLICATIONS

This application claims benefit of U. S. Provisional Application No. 60/036,858, filed Feb. 3, 1997.

BACKGROUND OF THE INVENTION

The present invention provides novel 2-methoxyimino-2-(pyridinyloxymethyl)phenyl acetamide compounds with carboxylic acid substituents on the pyridine ring, their use as fungicidal compounds, and their use in fungicidal compositions comprising at least one of the 2-methoxyimino-2-(pyridinyloxymethyl)phenyl acetamide compounds as the active ingredient.

SUMMARY OF THE INVENTION

This invention provides novel 2-methoxyimino-2-(pyridinyloxymethyl)phenyl acetamide compounds of formula (1), below

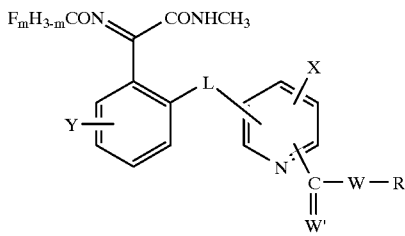

Formula (1)

wherein m is an integer 0–3;

Y is H, halogen, $C_{1-4}$ alkyl, $C_{1-4}$ alkoxy, or $C_{1-4}$ alkylthio;

X is H, $C_{1-6}$alkyl, $C_{1-6}$alkoxy, halo-$C_{1-6}$alkyl, halo-$C_{1-6}$ alkoxy, halo, nitro, carbo-$C_{1-6}$alkoxy, cyano, $C_{1-6}$alkylthio, or halo-$C_{1-6}$alkylthio;

W or W' is independently O or S;

R is H, $C_{1-6}$alkyl, or $C_{3-7}$cycloalkyl; optionally substituted by halo-$C_{1-6}$alkyl, halo-$C_{1-6}$alkoxy, $C_{2-6}$alkenyl, halo-$C_{2-6}$alkenyl, $C_{2-6}$alkynyl, -C≡N, $C_{1-6}$ alkoxy, halogen, aryl, substituted aryl, or heteroaryl; and L is —O—, —$CH_2$—, —$SO_n$—, —$CH_2O$—, —$OCH_2$—, —$CH_2S$—, —$SCH_2$—,

,

DETAILED DESCRIPTION OF THE INVENTION

Throughout this document, all temperatures are given in degrees Celsius and all percentages are weight percentages, unless otherwise stated.

The term "halogen" or "halo" refers to F, Cl, I, or Br.

The term "alkyl", "alkenyl", or "alkynyl" refers to a straight chain or branched chain carbon radical containing the designated number of carbon atoms.

The term "alkoxy" refers to a straight or branched chain alkoxy group.

The term "halo alkyl" refers to a straight or branched alkyl group substituted with one or more halo atoms. The term "halo alkoxy" refers to an alkoxy group substituted with one or more halo atoms.

The term "aryl" or "Ph" refers to a phenyl group. The term "substituted aryl" refers to a phenyl group substituted with $C_{1-6}$alkyl, $C_{1-6}$alkoxy, halo-$C_{1-6}$alkyl, halo-$C_{1-6}$alkoxy, halo, nitro, carbo-$C_{1-6}$alkoxy, or cyano. The term "heteroaryl" refers to pyridyl, pyridinyl, pyrazinyl or pyridazinyl.

The term "Me" refers to a methyl group. The term "Et" refers to an ethyl group. The term "Pr" refers to a propyl group. The term "Bu" refers to a butyl group.

The term "EtOAc" refers to ethyl acetate.

The term "ppm" refers to parts per million. The term, "psi" refers to pounds per square inch.

The term "M.P." refers to melting point. The term "bp" refers to boiling point.

While all the compounds of this invention have fungicidal activity, certain classes of compounds may be preferred for reasons such as, for example, greater efficacy or ease of synthesis.

A preferred class includes those compounds of Formula (2), below

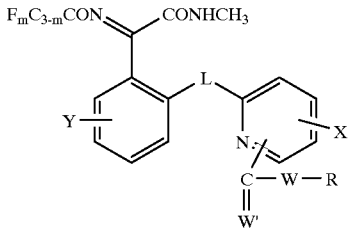

Formula (2)

wherein the substituents are as defined in Formula (1), above.

A more preferred class includes those compounds of Formula (3), below

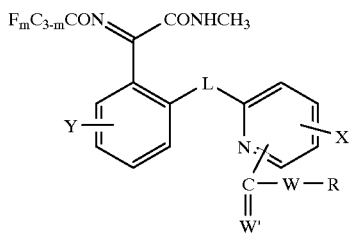

Formula (3)

wherein Y is halogen and the remaining substituents are as defined in Formula (1), above.

A next more preferred class includes those compounds of Formula (4), below

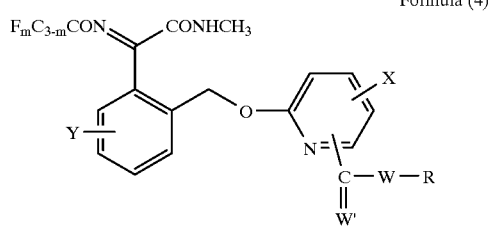

Formula (4)

wherein the substituents are as defined in Formula (1), above.

A next more preferred class includes those compounds of Formula (5), below

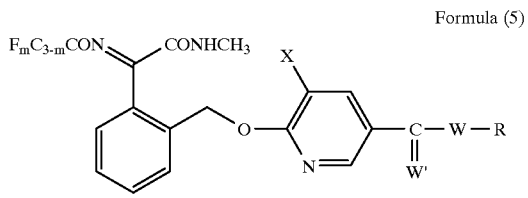

Formula (5)

wherein the substituents are as defined in Formula (1), above.

A next more preferred class includes those compounds of Formula (5) wherein X is $C_{1-4}$ alkyl, halo, or halo-$C_{1-4}$ alkyl, and R is $C_{1-4}$ alkyl, optionally substituted by alkenyl, alkynyl, or alkoxy.

The compounds of this invention are made using well known chemical procedures. The required starting materials are commercially available, or readily synthesized utilizing standard procedures.

The compounds of formula (1) are, in general, prepared by treatment of about equimolar amounts of the corresponding pyridine with the corresponding hydroxymethyl-methoxyimino-benzeneacetamide to which was added an about equimolar amount or slight excess molar amount of a strong base, such as, for example, sodium hydride, in the presence of an inert solvent. The compound of formula (1) thus produced may optionally be modified by subsequent reaction to other desired compounds of formula (1).

The following examples further illustrate this invention. The examples should not be construed as limiting the invention in any manner.

EXAMPLES

Example 1

5-Bromo-2-fluoro-3-methyl pyridine

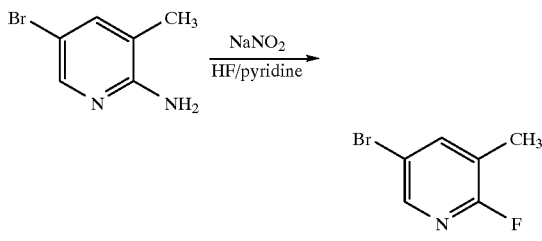

To a solution of HF/pyridine (50 g) at −5° C. in a plastic beaker equipped with a magnetic stirrer was added 2-amino-5-bromo-3-methyl pyridine (7.55 g, 40.3 mmol) over a ten minute period. Sodium nitrite (3.06 g, 44.4 mmol) was added over a 15 minute period to this reaction mixture, maintaining the temperature below 10° C. After stirring for one hour, the reaction mixture was poured into ice (100 g). The solid obtained was filtered and washed with cold water. The dried solid was dissolved in dichloromethane, dried (anhydrous $Na_2SO_4$), filtered and concentrated in vacuo to give 5-bromo-2-fluoro-3-methyl pyridine (7.2 g) as an off-white solid. M.P. 64–65° C.

Example 2

3-Bromo-2-fluoro-5-methyl pyridine

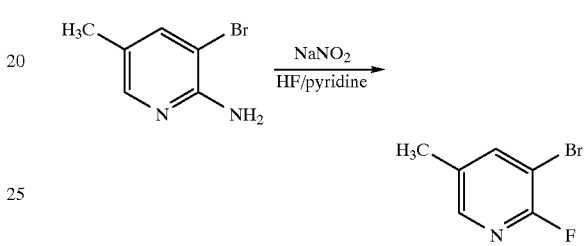

Utilizing the general procedure described in Example 1 and starting from 2-amino-3-bromo-5-methylpyridine gave 3-bromo-2-fluoro-5-methyl pyridine (5.6 g) as a white solid.

Example 3

6-Fluoro-5-methyl-nicotinic acid: methyl ester

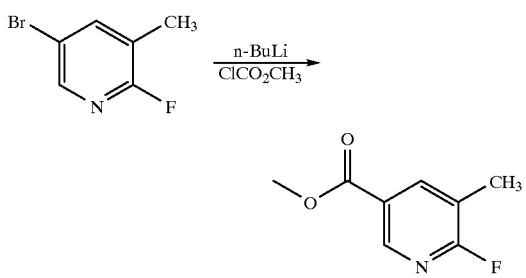

To a solution of the product of Example 1 (2.0 g, 105 mmol) in tetrahydrofuran (THF) (40 mL), was added n-BuLi (7.2 mL, 1.6 M in hexane) at −78° C. and the mixture was stirred for 15 minutes under $N_2$ atmosphere. The resulting suspension was added dropwise via cannula to a solution of methyl chloroformate in THF (20 mL) at −78° C. The reaction was warmed to −25° C. and stirred for one hour. After warming to 0° C., water was added and the mixture extracted with ether (3×50 mL), dried (anhydrous $Na_2SO_4$), filtered and concentrated in vacuo. The crude thick oil was chromatographed (silica gel, 33% EtOAc/Hexane) to give methyl (2-fluoro-3-methyl-5-pyridine)ester (0.9 g) as a white flaky solid. M.P. 99–100° C.

Example 4

6-Fluoro-5-methyl-nicotinic acid: t-butyl ester

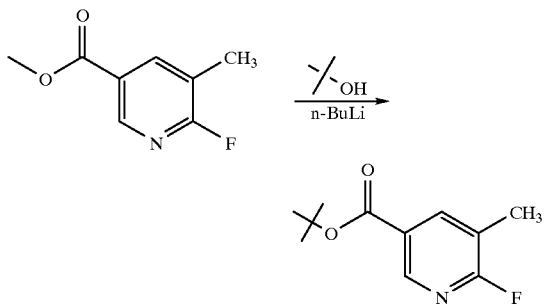

To a solution of t-butanol (0.19 g, 2.6 mmol) in THF (10 mL) was added n-BuLi (1.6 mL, 1.6M in hexane) at −70° C. under $N_2$ atmosphere. A solution of the product of Example 3 (0.4 g, 2.4 mmol) was added slowly to this mixture and stirred at −70° C. for one hour. The resulting suspension was warmed to 25° C. and stirred for 16 hours, quenched with water (10 mL) and the layers separated. The aqueous layer was extracted with ether (3×30 mL), dried (anhydrous $Na_2SO_4$), filtered and concentrated in vacuo to give t-butyl (2-fluoro-3-methyl-5-pyridine) ester (0.39 g) as a thick yellow oil.

Example 5

3-Trifluoromethyl-5-bromo-2-pyridinol

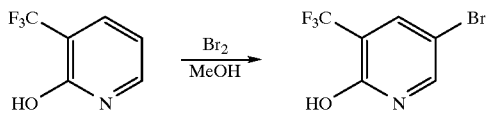

3-Trifluoromethyl-2-pyridinol (5.0 g, 0.031 mol) was dissolved with stirring in methanol (75 mL) and bromine (5.25 g, 0.033 mol) was added dropwise with cooling. The mixture was stirred overnight and evaporated to dryness. The residue was dissolved in ethyl acetate (250 mL), washed twice with water and brine, dried over sodium sulphate and evaporated to dryness. Chromatography over silica (20% ethyl acetate:80% hexane) gave 3-trifluoromethyl-5-bromo-2-pyridinol (5.2 g) as a cream solid. M.P. 160–162° C.

Example 6

2-Chloro-3-trifluoromethyl-5-bromopyridine

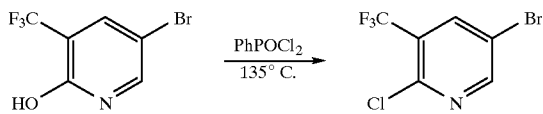

The product of Example 5 (11.5 g, 0.048 mol) and phenylphosphoryl dichloride (45 mL) were heated with stirring at 135° C. for four hours and allowed to cool to room temperature. The reaction mixture was poured onto ice (750 g) and allowed to warm to room temperature. The mixture was extracted with dichloromethane (150 mL) and filtered. The organic phase was separated, washed with water and 10% sodium carbonate solution and dried over anhydrous sodium sulphate. Evaporation of the solvent gave 2-chloro-3-trifluoromethyl-5-bromopyridine (11.6 g) as a yellow oil.

Example 7

2-Methylthio-3-trifluoromethyl-5-bromopyridine

The product of Example 6 (3.0 g, 0.012 mol) was dissolved with stirring in dimethyl sulphoxide (30 mL) and sodium methanethiolate (1.2 g, 0.017 mol) was added. The mixture was stirred at room temperature overnight, poured into ice-water, and extracted with hexane (2×50 mL). The organic extracts were combined, washed with water and brine, and dried over anhydrous sodium sulphate. Evaporation of the solvent under reduced pressure and purification of the residue by chromatography over silica (10% ethyl acetate:hexane) gave 2-methylthio-3-trifluoromethyl-5-bromopyridine (2.2 g) as a clear oil.

Example 8

6-Methylthio-5-trifluoromethyl-nicotinic acid: isopropyl ester

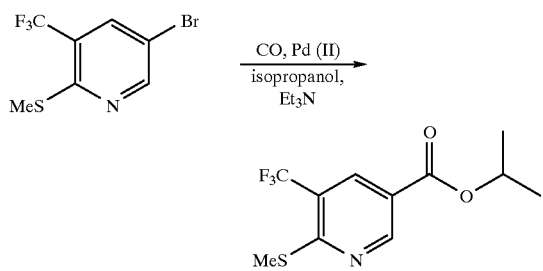

The product of Example 7 (2.0 g, 7.4 mmol) was dissolved in a mixture of isopropanol (8 mL) and triethylamine (4 mL) in a 45 mL Hastelloy bomb. Bis(triphenylphosphine) palladium (II) chloride (0.1 g) was added and the vessel charged with carbon monoxide to a pressure of 300 psi. The reaction mixture was heated to 130° C. for 17 hours, allowed to cool to room temperature, and the pressure released. The reaction mixture was diluted with ethyl acetate (25 mL), filtered, and the solvents evaporated under reduced pressure. The residual oil was dissolved in ethyl acetate (50 mL) and washed with water and brine. Evaporation of the solvent under reduced pressure and purification of the resultant oil by chromatography over silica (5% ethyl acetate:hexane) gave 6-methylthio-5-trifluoromethyl-nicotinic acid: isopropyl ester as a clear oil (1.8 g).

Example 9

6-Methylsulphonyl-5-trifluoromethyl-nicotinic acid: isopropyl ester

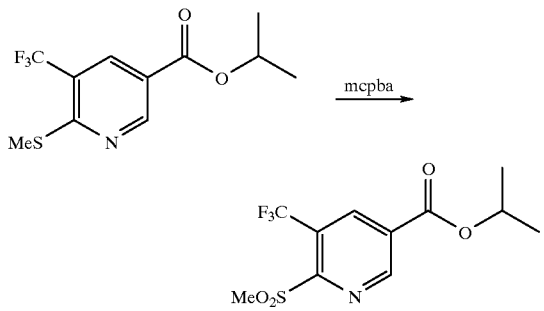

The product of Example 8 (1.8 g, 6.4 mmol) was dissolved with stirring in dichloromethane (100 mL) and m-chloroperoxybenzoic acid (55% pure, 4.4 g, 0.014 mol) was added. The mixture was stirred at room temperature overnight, 10% sodium carbonate solution (100 mL) was added, and the mixture was stirred vigorously for one hour. The phases were separated, and the organic phase was washed with 2M sodium hydroxide solution (50 mL) and brine. This was dried and the solvent evaporated under reduced pressure to give 5-trifluoromethyl-6-methylsulphonyl-nicotinic acid, isopropyl ester (1.8 g) as a clear oil which solidified on standing.

Example 10

3,5,6-Trichloropicolinic acid: isopropyl ester

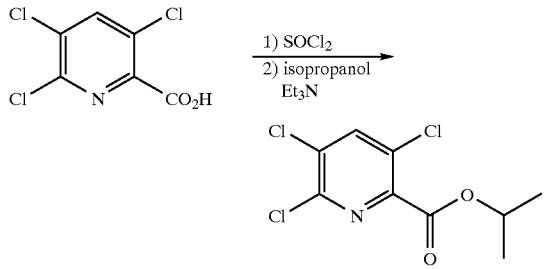

3,5,6-Trichloropicolinic acid (3.0 g, 0.013 mol) was slurried in thionyl chloride (20 mL) and dimethylformamide (5 drops) was added. The mixture was heated under reflux for three hours and allowed to cool. Evaporation of the solvent under reduced pressure gave the crude acid chloride as a yellow oily solid. This was dissolved in isopropanol (20 mL) and triethylamine (1.5 g, 0.015 mol) was added. The mixture was allowed to stir at room temperature overnight, poured into water (100 mL) and extracted with ethyl acetate (50 mL). The organic phase was separated, washed with water and brine, and dried over anhydrous sodium sulphate. Evaporation of the solvent under reduced pressure gave a gold oil which was filtered through a short column of silica, eluting with 5% ethyl acetate:hexane. Evaporation of the solvent under reduced pressure gave 3,5,6-trichloropicolinic acid; isopropyl ester (2.5 g) as a clear oil.

Example 11

2,5,6-Trichloronicotinic acid

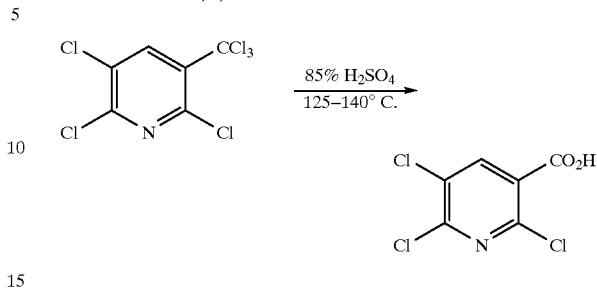

2,5,6-Trichloro-3-trichloromethylpyridine (22.5 g, 75 mmol) was suspended in 100 mL of 85% $H_2SO_4$ and heated to 125–140° C. for three hours. The solution was cooled to ambient temperature and poured over 1 kg of crushed ice. The resulting tan solid was filtered and recrystallized from hexane to give 2,5,6-trichloronicotinic acid (11.8 g) as tan crystals.

Example 12

2,5,6-Trichloronicotinic acid: t-amyl ester

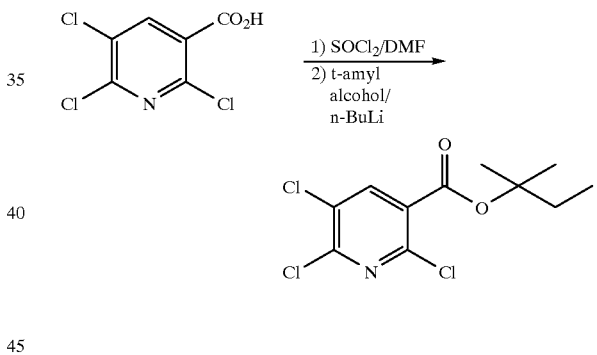

The product of Example 11 (2.5 g, 11 mmol) was slurried in thionyl chloride (30 mL) containing 2 drops of dry dimethylformamide (DMF). The slurry was heated to reflux at which time all components fully dissolved into solution. Reflux was continued for an additional three hours. After cooling to ambient temperature, the excess thionyl chloride was removed in vacuo and the resulting oily residue was taken up in diethyl ether ($Et_2O$) (20 mL) and cooled to 0° C. in an ice bath. A solution of t-amyl alcohol (0.88 g, 10 mmol) in $Et_2O$ (15 mL) was cooled to −10° C. in a dry ice bath and n-butyllithium (1.6 M solution in hexanes, 6.5 mL, 1 eq) was added dropwise over 10 minutes, keeping the temperature below 0° C. The solution was warmed to ambient temperature, charged to an addition funnel under nitrogen and added dropwise to the nitrogen-purged ethereal solution of the acyl chloride prepared above. After complete addition, the solution was warmed to ambient temperature with stirring overnight. The solution was washed with saturated brine (3×200 mL) and the organics were dried over $Na_2SO_4$, filtered, and the solvent removed in vacuo to give t-amyl 2,5,6-trichloronicotinate (92.46 g) as an orange oil.

Example 13

3-Chloro-6-methylthio-picolinic acid: t-butyl ester

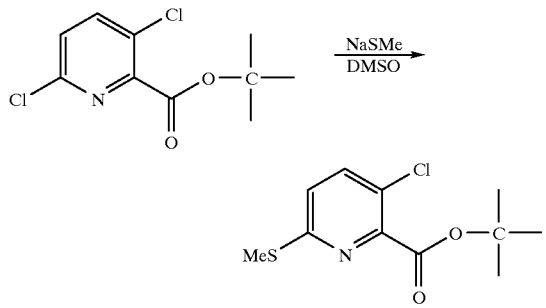

3,6-Dichloropicolinic acid: t-butyl ester (1.5 g, 6 mmol) was dissolved in dimethylsulfoxide (DMSO) (20 mL). To this solution was added sodium thiomethoxide (0.63g, 9 mmol) over 5 minutes, keeping the reaction below 30° C. Work up and purification of the mixture by chromatography gave the desired product (0.9 g) as a clear oil.

Example 14

3-Chloro-6-methylsulphonylpicolinic acid: t-butyl ester

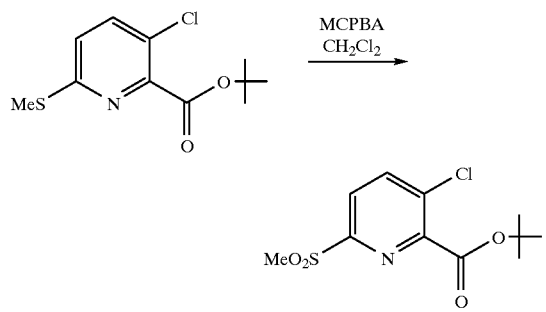

A 50 mL round bottom flask equipped with a magnetic stirring bar was charged with (0.90 g, 0.003 mol) 3-chloro-6-methylthiopicolinic acid: t-butyl ester and 15 mL $CH_2Cl_2$. The solution was cooled to 0° C., and (2.23 g, 0.06 mol) m-chloroperoxybenzoic acid added over approximately three minutes. The reaction was allowed to warm to room temperature and stirred overnight. The mixture was diluted with 35 mL $CH_2Cl_2$ and washed twice with 20 mL portions of 2N NaOH, three times with 20 mL portions of water, then dried ($Na_2SO_4$). The solvent was evaporated under reduced pressure to give 3-chloro-6-methylsulphonylpicolinic acid: t-butyl ester (0.9 g) as a clear oil.

Example 15

(2-Chloro-6-methyl)isonicotinic acid: methyl ester

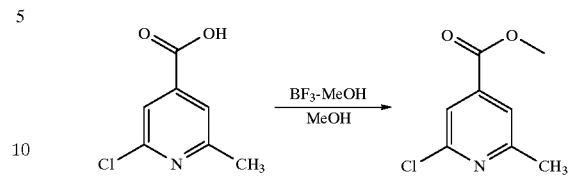

2-Chloro-6-methyl-4-pyridine carboxylic acid (0.25 g, 1.46 mmol) was dissolved in 10 mL methanol under nitrogen, followed by the dropwise addition of $BF_3$.MeOH (0.45 mL, 3 eq) via syringe. The solution was refluxed for three hours, then stirred at room temperature overnight. The solution was poured into 20 mL water and extracted with $Et_2O$ (2×25 mL). The organics were collected, washed with 1.0 N NaOH, $H_2O$, dried over $MgSO_4$, then concentrated to give methyl (2-chloro-6-methyl)isonicotinate (0.14 g) as a peach colored solid.

Example 16

5,6-Dichloronicotinic acid: isopropyl ester

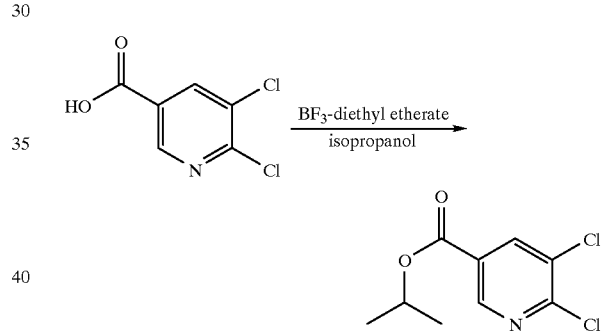

5,6-Dichloronicotinic acid (2.00 g, 10.4 mmol) was dissolved in 50 mL isopropanol to which was added $BF_3$-diethyl etherate (3.84 mL, 3 eq). The solution was refluxed overnight. When cooled, the solution was poured into 100 mL water and extracted with $Et_2O$ (2×100 mL) The organics were collected, washed with water, brine, 1.0 N NaOH, dried over $MgSO_4$, and concentrated to give isopropyl 5,6-dichloronicotinate (0.62 g) as a cream solid.

Example 17

5,6-Dichloronicotinic acid: (dimethyl)propargyl ester

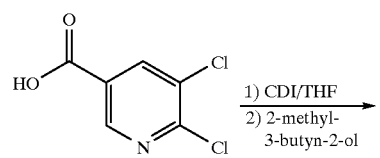

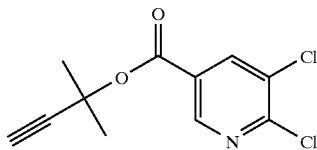

5,6-Dichloronicotinic acid (1.92 g, 10.0 mmol) was slurried in 10 mL tetrahydrofuran to which carbonyldiimidazole (CDI) (1.78 g, 11.0 mmol) was added. The mixture was stirred at 40° C. for one hour to a uniform solution. 2-Methyl-3-butyn-2-ol (1.01 g, 12.0 mmol) was added via pipette and the solution refluxed overnight. The solution was poured into 4–5 volumes of water and extracted with Et$_2$O (2×100 mL). The organics were washed with 2.0 N NaOH, dried over MgSO$_4$, and concentrated to 1.2 g pale yellow oil. Crude product was chromatographed on medium column using silica gel (23–400 mesh) with descending solvent gradient from 100% petroleum ether to 50/50 pet. ether/ethyl acetate as the mobile phase. Elution and concentration gave (dimethyl)propargyl 5,6-dichloronicotinate (0.50 g) as a colorless oil.

Example 18

5,6-Dichloronicotinic acid: linalooyl ester

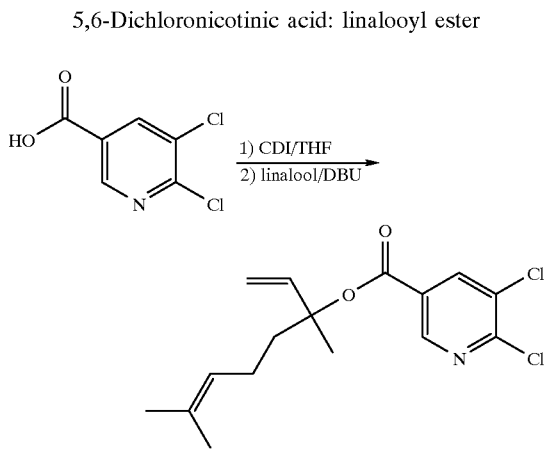

5,5-Dichloronicotinic acid (1.78 g, 10.0 mmol) was dissolved in 10 mL tetrahydrofuran to which carbonyldiimidazole (1.78 g, 11.0 mmol) was added. The solution was stirred at room temperature for one hour and linalool (1.85 g, 12.0 mmol) was added along with 1,8-diazabicyclo[5.4.0]undec-7-ene (1.67 g, 11.0 mmol). The solution was refluxed for three hours then cooled to room temperature, poured into 4–5 volumes of water and extracted with Et$_2$O (2×100 mL). The organics were dried over MgSO$_4$ and concentrated to 1.65 g amber oil. Crude product was chromatographed on medium column using silica gel (230–400 mesh) with descending solvent gradient from 100% petroleum ether to 80/20 petroleum ether/ethyl acetate as the mobile phase. The desired product, 5,6-dichloronicotinic acid; linalooyl ester, was eluted and concentrated (0.50 g) as a yellow oil.

Example 19

1-Chloro-3-fluoro-2-[(1,1-dimethylethoxy)methyl]benzene

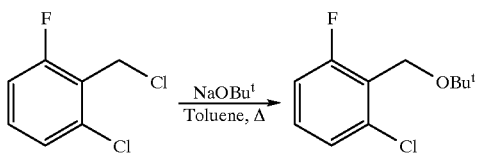

A mixture of 200 g (1.117 mole) of 2-chloro-6 fluorobenzyl chloride, 118 g (1.23 mole) of sodium t-butoxide, 2.2 mL (11 mmole) of 15-crown-5 (15-C-5) and 1.2 L of toluene was heated at reflux temperature for four hours. After allowing the reaction mixture to cool to 45° C., 600 mL of water was added followed by 90 mL of 2N HCl. After separation, the organic phase was concentrated in vacuo to give a dark oil. Distillation using a 5-tray Oldershaw column, sand bath to 155° C., gave 217.5 g of 1-chloro-3-fluoro-2-[(1,1-dimethylethoxy)methyl]-benzene as a clear liquid (bp 60–64° C./0.6 mm Hg.).

Example 20

1,3-Dichloro-2-[(1,1-dimethylethoxy)methyl]benzene

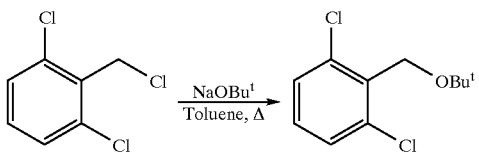

Utilizing the general procedure described in Example 19 and starting from 2,6-dichlorobenzyl chloride gave 1,3-dichloro-2-[(1,1-dimethylethoxy)methyl]benzene (92% yield, bp 74–75° C./0.01 mm Hg.).

Example 21

Ethyl 3-fluoro-2-[(1,1-dimethylethoxy)methyl]-α-oxo-benzeneacetate

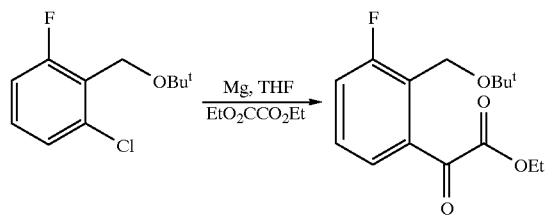

To a mixture of 73 g (3.0 mole, 3 eq) of magnesium turnings in 700 mL of THF was added 40 g (0.25 mole) of 1-chloro-3-fluoro-2-[(1,1-dimethylethoxy)-methyl]benzene followed by 1 mL of 1,2-dibromoethane. The reaction mixture was heated at reflux temperature and over the next four hours another 1 mL of 1,2-dibromoethane was added in two portions. At the end of that time period, gas chromatography indicated Grignard formation had commenced. The remaining 177 g of the chlorofluorobenzene added over one hour, and the mixture was heated at reflux temperature for an additional 12 hours. The resulting cloudy dark brown mixture was cooled to 5° C. with an ice-bath and was added via nitrogen pressure cannulation to a solution of 163 mL (1.2 mole) of diethyloxalate in 300 mL of THF. The temperature during addition was maintained between −60° and −50° C. via dry ice/acetone bath cooling, and the addition was complete in 45 minutes. After allowing the mixture to warm to 0° C., 100 mL of 2N HCl was added, followed by 200 mL of water and concentrated HCl to bring the pH to 2. The THF was removed in vacuo, EtOAc was added, and the mixture washed with water, brine, and concentrated in vacuo to give a dark liquid. Distillation using a 5-tray Oldershaw column gave 172 g of ethyl 3-fluoro-2-[(1,1-dimethylethoxy)methyl]-α-oxo-benzeneacetate as a light yellow oil (bp 113–117° C./0.35 mm Hg.).

Example 22

Ethyl 3-chloro-2-[(1,1-dimethylethoxy)methyl]-α-oxo-benzeneacetate

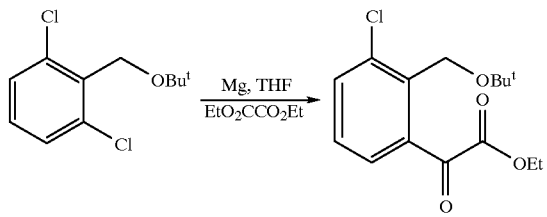

Utilizing the general procedure described in Example 21 and starting from 1,3-dichloro-2-[(1,1-dimethylethoxy)methyl]benzene gave ethyl 3-chloro-2-[(1,1-dimethylethoxy)methyl]-α-oxo-benzeneacetate (bp 127–130° C./0.1 mm Hg.).

Example 23

Ethyl 3-fluoro-2-[(1,1-dimethylethoxy)methyl]-α-(methoxyimino)-benzeneacetate

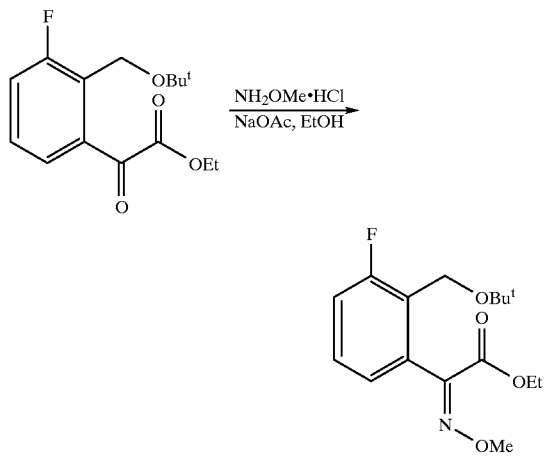

To a solution of 79 g (0.28 mole) of ethyl 3-fluoro-2-[(1,1-dimethylethoxy)methyl]-α-oxo-benzeneacetate in 300 mL of ethyl alcohol was added 100 mL (0.39 mole, 30% aq) of methoxylamine HCl followed by 33 g (0.4 mole) of sodium acetate. The mixture was then heated at 60° C. for three hours. After cooling to room temperature, the salts were filtered and the mixture was concentrated in vacuo. Water and EtOAc were added, the layers separated, and the organics were washed with saturated NaHCO₃, brine and dried over MgSO₄. After filtration, the solution was concentrated in vacuo to give 86.1 g of ethyl 3-fluoro-2-[(1,1-dimethylethoxy)methyl]-α-(methoxyimino)-benzeneacetate as a lightly tinted oil, 1:2 ratio of oxime isomers by gas chromatography.

Example 24

Ethyl 3-chloro-2-[(1,1-dimethylethoxy)methyl]-α-(methoxyimino)-benzeneacetate

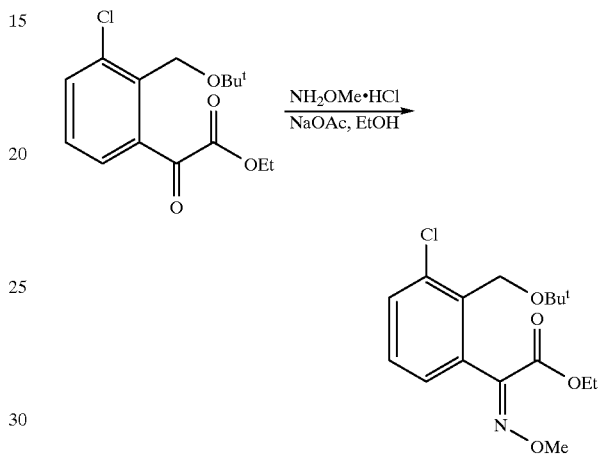

Utilizing the general procedure described in Example 23 and starting from ethyl 3-chloro-2-[(1,1-dimethylethoxy)methyl]-α-oxo-benzeneacetate, gave ethyl 3-chloro-2-[(1,1-dimethylethoxy)methyl]-α-(methoxyimino)-benzeneacetate.

Example 25

(E),(Z)-3-Fluoro-2-(hydroxymethyl)-α-(methoxyimino)-N-methyl-benzeneacetamide

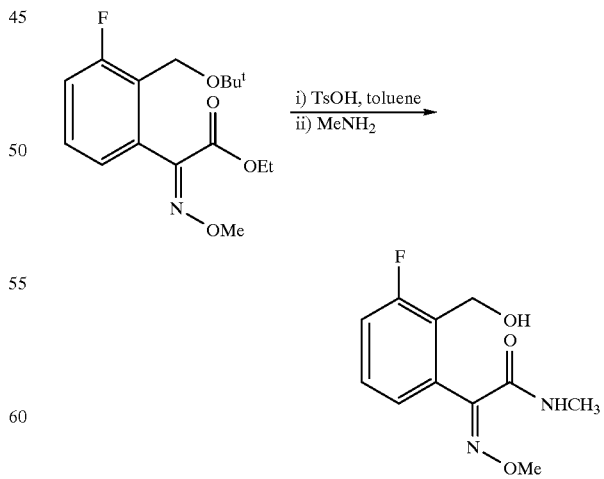

To a solution of 84 g (270 mmole) of ethyl 3-chloro-2-[(1,1-dimethylethoxy)methyl]-α-(methoxyimino)-benzeneacetate in 250 mL of toluene was added 10.3 g (54 mmole) of p-toluenesulfonic acid monohydrate, and the mixture was heated to reflux temperature (90° C.). Initial vigorous off-gasing occurred, and after three hours, GC indicated the reaction was complete. The solution was cooled to room temperature and 30 mL (340 mmole) of 40% aqueous methylamine was added. The temperature of the reaction went from 25° C. to 38° C. with a cloudy solid forming. The mixture was allowed to stir at room temperature overnight. The solid was filtered, washed with toluene and vacuum oven dried at 40° C. to give 57.8 g of (E),(Z)-3-fluoro-2-(hydroxymethyl)-α-(methoxyimino)-N-methyl-benzeneacetamide as a white crystalline solid. M.P. (softens) 147–151° C.

Example 26

(E),(Z)-3-Chloro-2-(hydroxymethyl)-α-(methoxyimino)-N-methyl-benzeneacetamide

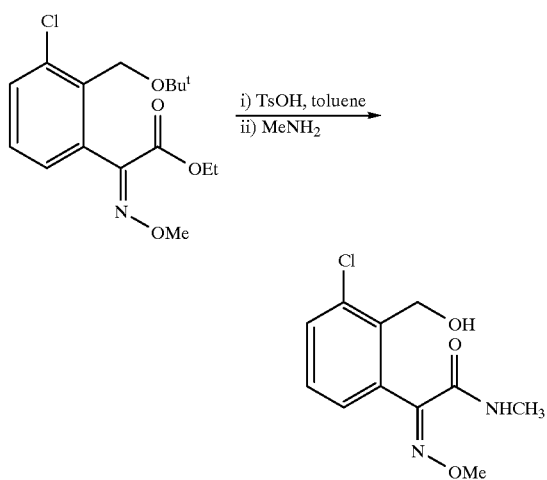

Utilizing the general procedure described in Example 25 and starting from ethyl 3-chloro-2-[(1,1-dimethylethoxy)methyl]-α-(methoxyimino)-benzeneacetate gave (E),(Z)-3-chloro-2-(hydroxymethyl) -α-(methoxyimino)-N-methyl-benzeneacetamide. M.P. 141–143° C.

Example 27

α-(Methoxyimino)-N-methyl-2-[[[5-chloro-6-(t-butoxycarbonyl)-2-pyridinyl]oxy]methyl]-benzeneacetamide

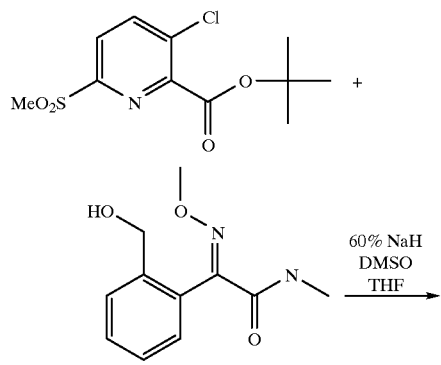

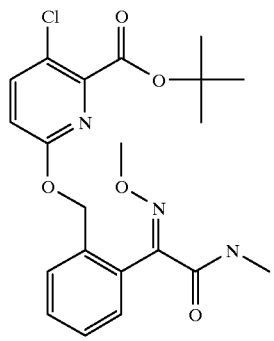

A 50 mL 3-neck round bottom flask equipped with a magnetic stirring bar and N₂ inlet was charged with (0.55 g, 0.0024 mol) 2-hydroxymethyl-α-methyoxyimino-N-methyl-benzeneacetamide and 10 mL anhydrous THF. To the reaction was added (0.14 g, 0.003mol) 60% NaH with stirring under nitrogen for 20 minutes. To the reaction was then added 3-chloro-6-methylsulphonylpicolinic acid: t-butyl ester (0.900 g, 0.003 mol) dissolved in 8 mL anhydrous THF, then 2 mL DMSO and stirring for three hours under nitrogen at room temperature. The mixture was then diluted with 20 mL ethyl acetate and 50 mL DI water and extracted four times with 20 mL portions of ethyl acetate. The combined organic extracts were washed three times with 50 mL portions DI water and twice with 25 mL portions brine to give the resulting product, α-(methoxyimino)-N-methyl-2-[[[5-chloro-6-(t-butoxycarbonyl)-2-pyridinyl]oxy]methyl]-benzeneacetamide, as an off-white oily solid after chromatography. M.P. 103–108° C.

Example 28

α-(Methoxyimino)-N-methyl-2-[[[5-bromo-3-methyl-2-pyridinyl]oxy]methyl]-benzeneacetamide

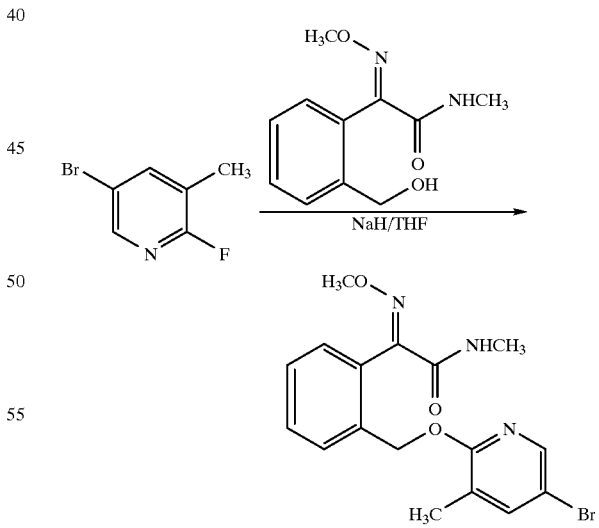

Sodium hydride (60%, 0.18 g, 4,5 mmol) was added to a solution of 2-hydroxymethyl-α-methyoxyimino-N-methyl-benzeneacetamide (1.0 g, 4.5 mmol) in dry THF (25 mL) and stirred for 10 minutes at 25° C. under N₂ atmosphere. The pyridine product of Example 1 (0.86 g, 4.5 mmol) was added to this reaction mixture and stirred for 16 hours. Water (20 mL) was added and the resulting mixture was extracted with ether (3×50 mL), dried (anhydrous Na₂SO₄), filtered and concentrated in vacuo to yield crude residue (1.5 g), which was then triturated with ether/pentane to give α-(methoxyimino)-N-methyl-2-[[[5-bromo-3-methyl-2-pyridinyl]oxy]methyl]-benzeneacetamide (1.1 g) as a white solid. M.P. 115–116° C.

Example 29

α-(Methoxyimino)-N-methyl-2-[[[5-(isopropoxycarbonyl)-3-methyl-2-pyridinyl]oxy]methyl]-benzeneacetamide

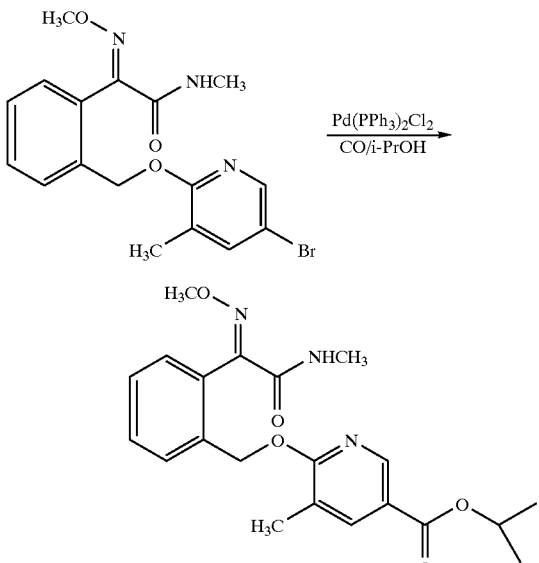

Carbon monoxide (200 psi) was charged into a 300 mL Parr reactor containing a suspension of the product of Example 28 (2.0 g, 5.1 mmol), Pd(PPh)₃Cl₂ (0.18 g, 10 mol %), and Et₃N (0.57 g, 5.6 mmol) in isopropanol (50 mL). This mixture was heated at 130° C. for 16 hours and heating was continued at 160° C. for 16 hours. After cooling, the mixture was filtered and concentrated. The residue was suspended in a mixture of ether (50 mL) and water (30 mL). The layers were separated and the aqueous layer was extracted with ether (2×50 mL), dried (anhydrous Na₂SO₄), filtered, and concentrated in vacuo. The brown residue was chromatographed (silica gel, 50% EtOAc/hexane) to give α-(methoxyimino)-N-methyl-2-[[[5-(isopropoxycarbonyl)-3-methyl-2-pyridinyl]oxy]methyl]-benzeneacetamide (0.7 g) as a tan solid. M.P. 101–102° C.

Example 30

α-(Methoxyimino)-N-methyl-2-[[[3-bromo-5-methyl-2-pyridinyl]oxy]methyl]-benzeneacetamide

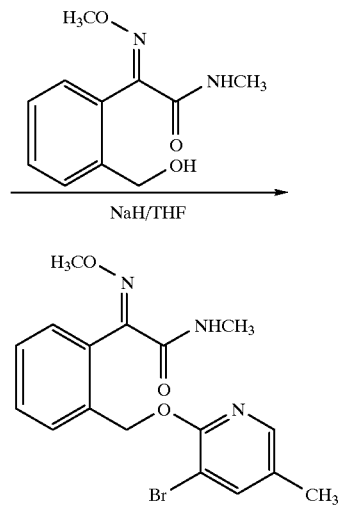

Utilizing the general procedure described in Example 28 gave α-(methoxyimino)-N-methyl-2-[[[3-bromo-5-methyl-2-pyridinyl]oxy]methyl]-benzeneacetamide (9.5 g) as an off-white solid. M.P. 104–105° C.

Example 31

α-(Methoxyimino)-N-methyl-2-[[[3-(isopropoxycarbonyl)-5-methyl-2-pyridinyl]oxy]methyl]-benzeneacetamide

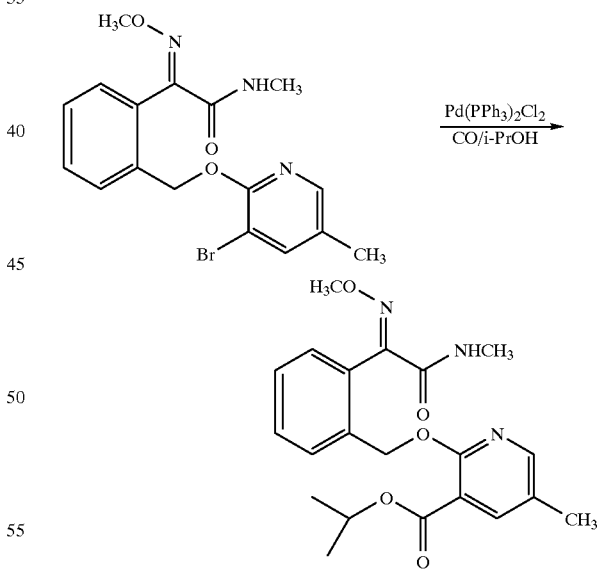

Utilizing the general procedure described in Example 29 gave α-(methoxyimino)-N-methyl-2-[[[3-(isopropoxycarbonyl)-5-methyl-2-pyridinyl]oxy]methyl]-benzeneacetamide (0.49 g) as a white solid. M.P. 165–166° C.

Example 32

α-(Methoxyimino)-N-methyl-2-[[[5-(t-butoxycarbonyl)-3-methyl-2-pyridinyl]oxy]methyl]-benzeneacetamide

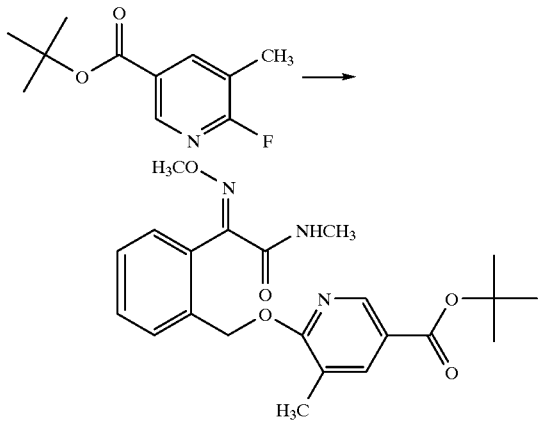

Utilizing the general procedure described in Example 28, but starting from 6-fluoro-5-methylnicotinic acid: t-butyl ester gave α-(methoxyimino)-N-methyl-2-[[[5-(t-butoxycarbonyl)-3-methyl-2-pyridinyl]oxy]methyl]-benzeneacetamide (0.49 g) as a white solid. M.P. 98–100° C.

Example 33

α-(Methoxyimino)-N-methyl-2-[[[5-(isopropoxycarbonyl)-3-trifluoromethyl-2-pyridinyl]oxy]methyl]-benzeneacetamide

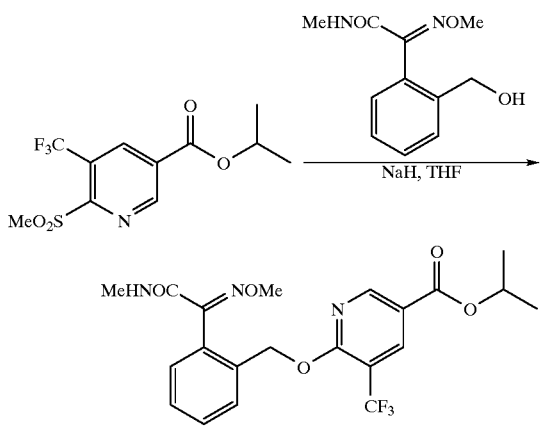

2-Hydroxymethyl-α-methyoxyimino-N-methyl-benzeneacetamide (1.0 g, 4.5 mmol) was dissolved with stirring in dry THF (30 mL) and sodium hydride (60% dispersion in mineral oil, 0.25 g, 6.25 mmol) was added. The mixture was stirred at room temperature for two hours and a solution of the product of Example 9 (1.4 g, 4.5 mmol) in dry THF (5 mL) was added. The mixture was stirred at room temperature overnight, poured into water, and extracted with ethyl acetate. The organic extract was washed with water and brine and dried over anhydrous sodium sulphate. Evaporation of the solvent under reduced pressure and purification of the residue by chromatography over silica (25% ethyl acetate:hexane) gave α-(methoxyimino)-N-methyl-2-[[[5-(isopropoxycarbonyl)-3-trifluoromethyl-2-pyridinyl]oxy]methyl]-benzeneacetamide (0.65 g) as a white solid.

Example 34

α-(Methoxyimino)-N-methyl-2-[[[3,5-dichloro-6-(isopropoxycarbonyl)-2-pyridinyl]oxy]methyl]-benzeneacetamide and α-(methoxyimino-N-methyl-2-[[[5,6-dichloro-2-(isopropoxycarbonyl)-3-pyridinyl]oxy]methyl]-benzeneacetamide

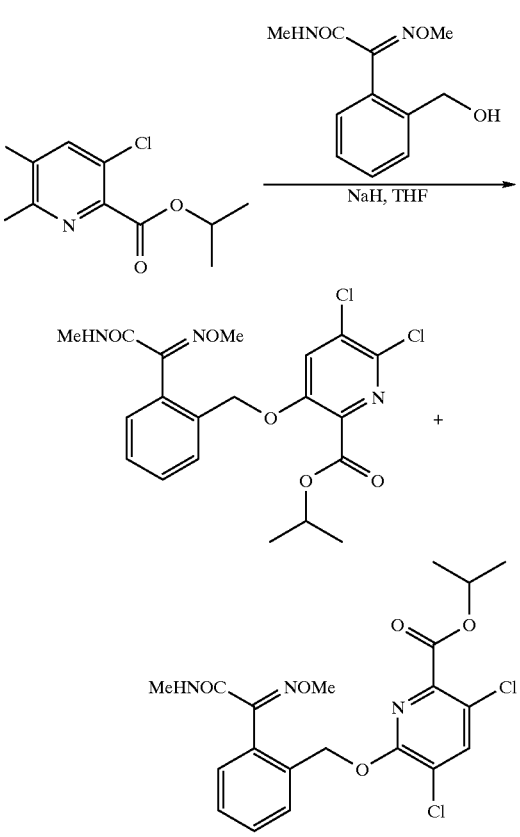

2-Hydroxymethyl-α-methyoxyimino-N-methyl-benzeneacetamide (1.0 g, 4.5 mmol) was dissolved with stirring in dry THF (30 mL) and sodium hydride (60% dispersion in mineral oil, 0.25 g, 6.25 mmol) was added. The mixture was stirred at room temperature for two hours and a solution of the product of Example 10 (1.2 g, 4.5 mmol) in dry THF (5 mL) was added. The mixture was stirred at room temperature overnight, poured into water, and extracted with ethyl acetate. The organic extract was washed with water and brine and dried over anhydrous sodium sulphate. Evaporation of the solvent under reduced pressure and purification of the residue by chromatography over silica (25% ethyl acetate:hexane) gave α-(methyoxyimino)-N-methyl-2-[[[3,5-dichloro-6-(carboisopropoxy)-2-pyridinyl]oxy]methyl]-benzeneacetamide (0.74 g) as a clear gum, and α-(methyoxyimino-N-methyl-2-[[[5,6-dichloro-2-(carboisopropoxy)-3-pyridinyl]oxy]methyl]-benzeneacetamide (0.52 g) as a clear oil.

Example 35

α-(Methoxyimino)-N-methyl-2-[[[3,6-dichloro-5-(1,1-dimethyl-1-propoxycarbonyl)-2-pyridinyl]oxy]methyl]-benzeneacetamide and α-(methoxyimino)-N-methyl-2-[[[5,6-dichloro-3-(1,1-dimethyl-1-propoxycarbonyl)-2-pyridinyl]oxy]methyl]-benzeneacetamide

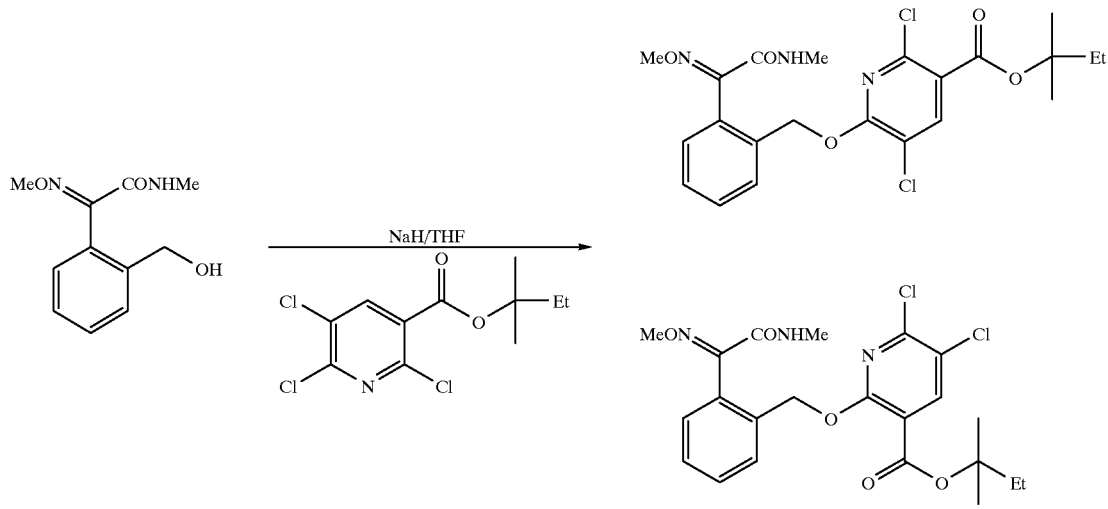

The product of Example 12 (1.8 g, 6 mmol) was added to a slurry containing 2-hydroxymethyl-α-methyoxyimino-N-methyl-benzeneacetamide (1.1 g, 5 mmol) and sodium hydride (0.25 g, 6 mmol) in dry THF (20 mL). After stirring at room temperature for 1.5 hours, the solution was diluted to 400 mL with deioinized water and extracted with $CH_2Cl_2$ (3×75 mL). The combined organic layers were washed with water, saturated brine, dried over $Na_2SO_4$, filtered, and concentrated to dryness. The residue was adsorbed on silica gel and the regioisomer products were separated by chromatography on silica gel using ethyl acetate in pentane. Chromatography resulted in giving α-(methoxyimino)-N-methyl-2-[[[5,6-dichloro-3-(1,1-dimethyl-1-propoxycarbonyl)-2-pyridinyl]oxy]methyl]-benzeneacetamide (130 mg), as a thick yellow oil, and α-(methoxyimino)-N-methyl-2-[[[3,6-dichloro-5-(1,1-dimethyl-1-propoxycarbonyl)-2-pyridinyl]oxy]methyl]-benzeneacetamide (1.4 g), as an orange oil.

Example 36

α-(Methoxyimino)-N-methyl-2-[[[3-chloro-6-(3-ethyl-3-pentoxycarbonyl)-2-pyridinyl]oxy]methyl]-benzeneacetamide

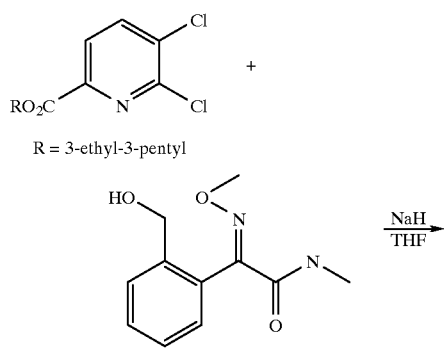

-continued

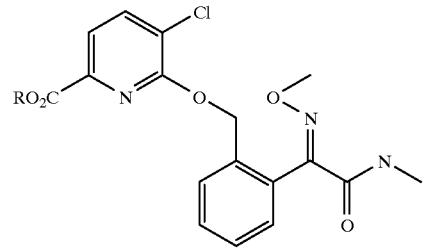

R = 3-ethyl-3-pentyl

NaH (60% dispersion in mineral oil, 0.24 g, 6.0 mmol) was added to a solution of 2-hydroxymethyl-α-methyoxyimino-N-methyl-benzeneacetamide (1.11 g, 5.0 mmol) in THF (50 mL). 5,6-Dichloropicolinic acid: 3-ethyl-3-pentyl ester (1.68 g, 5.5 mmol) was dissolved in THF (10 mL) and added slowly via pipet to this mixture. As the mixture was stirred at room temperature under $N_2$ for one hour, the reaction mixture transformed to a dark green solution. The reaction volume was increased to ca. 125 mL with ethyl acetate and washed with water and brine. The organic phase was evaporated in vacuo to provide the crude product which was chromatographed on medium pressure LC using increasing gradient of ethyl acetate in hexane (0–50%). Concentrating chromatographic fractions gave α-(methoxyimino)-N-methyl-2-[[[3-chloro-6-(3-ethyl-3-pentoxycarbonyl)-2-pyridinyl]oxy]methyl]-benzeneacetamide (0.29 g) as a yellow oil.

Example 37

α-(Methoxyimino)-N-methyl-2-[[[3-chloro-5-(isopropoxycarbonyl)-2-pyridinyl]oxy]methyl]-benzeneacetamide

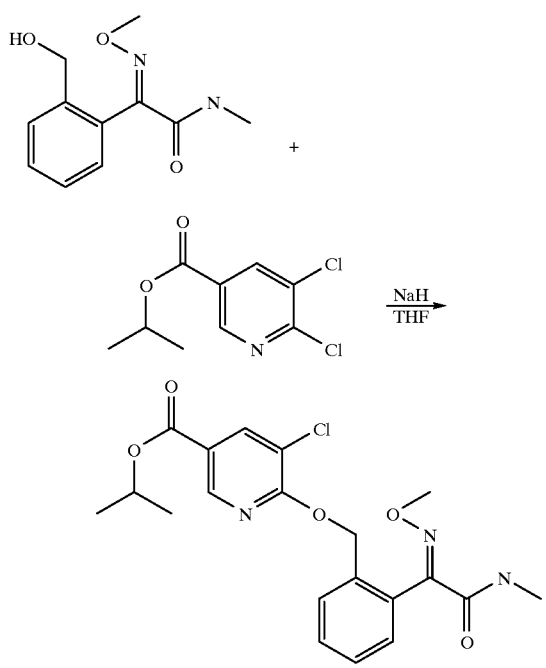

NaH (60% dispersion in mineral oil, 0.23 g, 12.0 mmol) was washed (2x) with hexanes then suspended in THF (10 mL) to which 2-hydroxymethyl-α-methyoxyimino-N-methyl-benzeneacetamide (0.89 g, 4.0 mmol) in THF solution was added. The solution was stirred at room temperature for 10 minutes at which time isopropyl-5,6-dichloronicotinate (1.00 g, 4.3 mmol) in THF solution was added. After 15 minutes of stirring at room temperature, the solution was poured into 4–5 volumes of water and extracted with $Et_2O$ (2×100 mL). The organics were dried over $MgSO_4$ and concentrated to 1.5 g tan, viscous oil. Crude product was chromatographed using silica gel (230–400 mesh) with descending solvent gradient from 100% petroleum ether to 80/20 petroleum ether/ethyl acetate as the mobile phase. Elution and concentration gave α-(methoxyimino)-N-methyl-2-[[[3-chloro-5-(isopropoxycarbonyl)-2-pyridinyl]oxy]methyl]-benzeneacetamide (0.72 g) as a white solid.

Example 38

α-(Methoxyimino)-N-methyl-2-[[[3-chloro-5-(carboxy)-2-pyridinyl]oxy]methyl]-benzeneacetamide

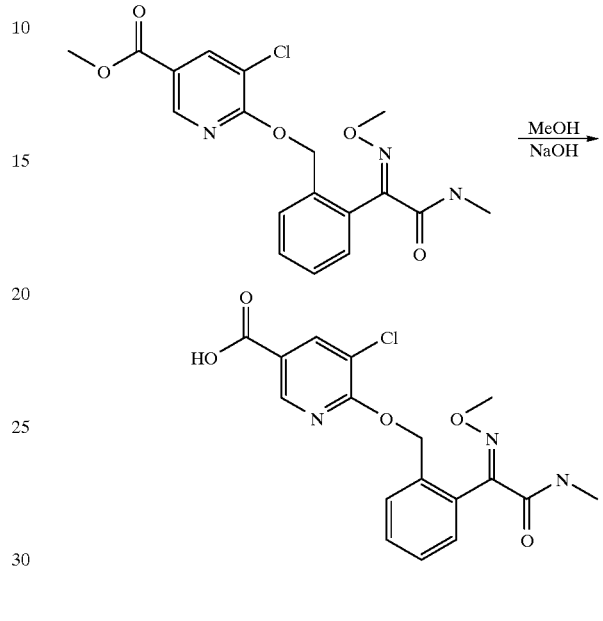

α-(Methoxyimino)-N-methyl-2-[[[3-chloro-5-(methoxycarbonyl)-2-pyridinyl]oxy]methyl]-benzeneacetamide (15.8 g, 40.4 mmol), prepared utilizing the general procedure described in Example 37, was dissolved in warm methanol (600 mL) to which was added 0.1 N NaOH (600 mL). The solution was stirred at room temperature overnight, then concentrated in vacuo to remove excess methanol. The remainder was extracted with $Et_2O$ (200 mL). The aqueous layer was acidified slightly (pH 5–6) resulting in a white precipitate. After 30 minutes of stirring at room temperature, the solid was collected, washed with water and dried in a vacuum oven to give α-(methoxyimino)-N-methyl-2-[[[3-chloro-5-(carboxy)-2-pyridinyl]oxy]methyl]-benzeneacetamide (14.9 g). M.P. 189–195° C.

Example 39

α-(Methoxyimino)-N-methyl-2-[[[3-chloro-5-(2,2,2-trifluoroethoxycarbonyl)-2-pyridinyl]oxy]methyl]-benzeneacetamide

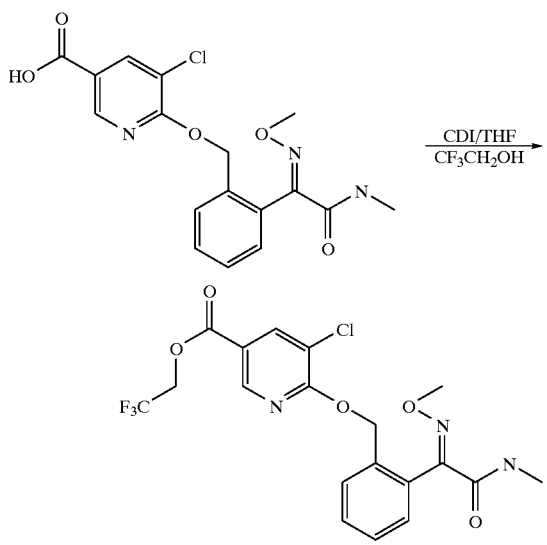

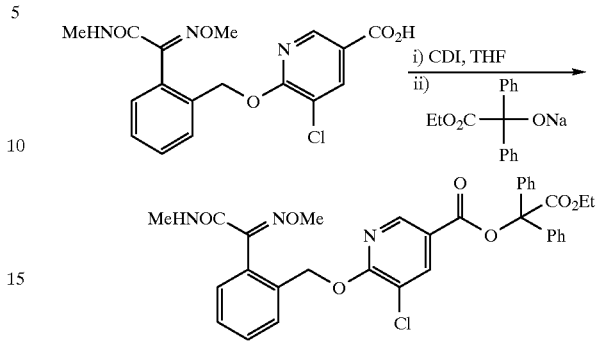

Example 40
α-(Methoxyimino)-N-methyl-2-[[[3-chloro-5-(ethoxycarbonyldiphenylmethoxycarbonyl)-2-pyridinyl]oxy]methyl]-benzeneacetamide The product of Example 38 (0.3 g, 0.79 mmol) was dissolved in THF (10 mL) to which carbonyldiimidazole (0.129 g, 0.79 mmol) was added. The solution was stirred at room temperature for one hour, at which time 2,2,2-trifluoroethanol (10 mL) was added and the solution stirred overnight at room temperature. The solution was poured into 4–5 volumes of water and extracted with Et₂O (2×100 mL). The organics were dried over MgSO₄ and concentrated to a yellow-brown oil (0.19 g). Crude product was chromatographed using silica gel (230–400 mesh) with descending solvent gradient from 100% petroleum ether to 80/20 petroleum ether/ethyl acetate as the mobile phase. Elution and concentration gave α-(methoxyimino)-N-methyl-2-[[[3-chloro-5-(2,2,2-trifluoroethoxycarbonyl)-2-pyridinyl]oxy]methyl]-benzeneacetamide (0.09 g) as a green oil.

The product of Example 38 (0.5 g, 1.32 mmol) was dissolved in 15 mL THF to which was added carbonyldiimidazole (0.24 g, 1.48 mmol). The solution was stirred at room temperature for one hour. NaH (60% dispersion in mineral oil, 0.08 g, 3.2mmol) was washed (2×) with hexanes then suspended in THF (10 mL) to which was added ethyl benzilate (0.40 g, 3.2 mmol). After 20 minutes, the imidazolide intermediate was added dropwise to the solution of alcoholic anion and stirring continued at room temperature overnight. The solution was poured into 4–5 volumes of water and extracted with Et₂O (2×100 mL). The organics were dried over MgSO₄ and concentrate to a yellow oil (0.60 g). Product was chromatographed on medium column using silica gel (230–400 mesh) with isocratic 80/20 petroleum ether/ethyl acetate as the mobile phase. Elution and concentration gave α-(methoxyimino)-N-methyl-2-[[[3-chloro-5-(ethoxycarbonyldiphenylmethoxycarbonyl)-2-pyridinyl]oxy]methyl]-benzeneacetamide (0.50 g) as a yellow solid.

Example 41
α-(Methoxyimino)-N-methyl-2-[[[3-chloro-5-(t-butylthio-carbonyl)-2-pyridinyl]oxy]methyl]-benzeneacetamide

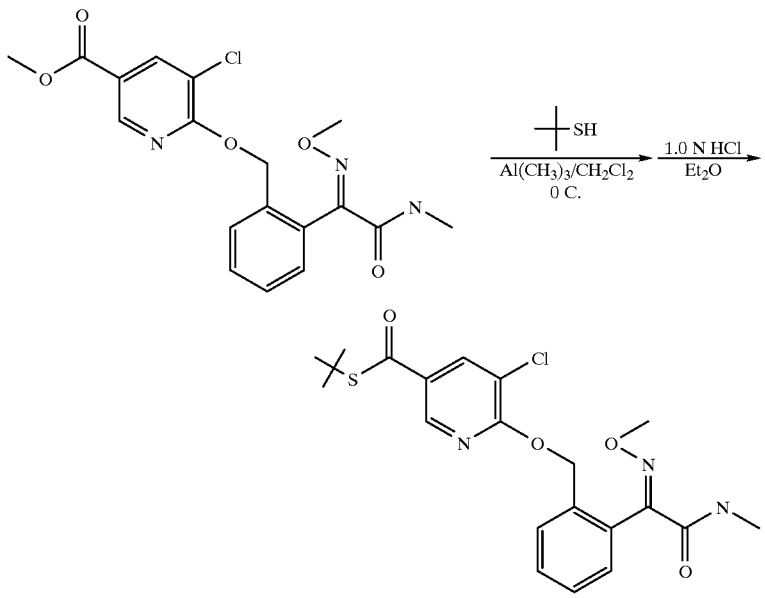

To a solution of 10.0 ml of trimethyl aluminum (2.0 M solution in toluene) in 40 ml of dry dichloromethane was added 2.2 ml of t-butyl mercaptan at 0° C. under nitrogen. The mixture was stirred and allowed to warm to room temperature over a 15–20 minute period. α-(Methoxyimino)-N-methyl-2-[[[3-chloro-5-(methoxycarbonyl)-2-pyridinyl]oxy]methyl]-benzeneacetamide (0.23 g) in 1 ml CH$_2$Cl$_2$ was added and the mixture was stirred for 20 hours at room temperature under nitrogen. Approximately 200 ml ether was added to the reaction and 1.0 N HCl was added cautiously until gas evolution ceased. The ether layer was separated, washed with 5% solution of NaOH, followed by water, and finally brine. The ether layer was dried and solvent removed in vacuo leaving a light oil. Oil was chromatographed on dry packed silica gel (230–400 mesh) with descending solvent gradient from 100% petroleum ether to 80/20 petroleum ether/ethyl acetate as the mobile phase. Elution and concentration gave α-(methoxyimino)-N-methyl-2-[[[3-chloro-5-(t-butylthiocarbonyl)-2-pyridinyl]oxy]methyl]-benzeneacetamide (0.150 g) as a solid material. M.P. 114–116.

Example 42

α-(Methoxyimino)-N-methyl-2-[[[3-chloro-5-(t-butoxycarbonyl)-2-pyridinyl]oxy]methyl]-3-fluoro-benzeneacetamide

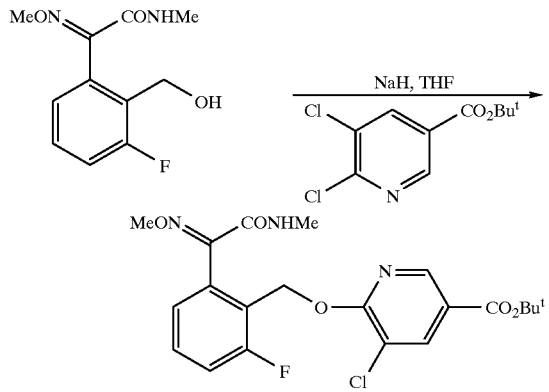

Sodium hydride (60%, 0.15 g, 3.7 mmol) was added to a solution of 3-fluoro-2-hydroxymethyl-α-methyoxyimino-N-methyl-benzeneacetamide (0.54 g, 2.25 mmol) in dry THF (10 mL) and stirred for 10 minutes at 25° C. under N$_2$ atmosphere. 5,6-Dichloronicotinic acid; t-butyl ester (0.59 g, 2.5 mmol) in 2–3 mL THF was added to this reaction mixture and stirred at 25° C. for about 2 hours. Water (40 mL) was added and the resulting mixture was extracted with ether (2×), dried (anhydrous Na$_2$SO$_4$), filtered and concentrated in vacuo to yield 1.2 g crude oil. Oil was chromatographed with dry pack silica gel (230–400 mesh) with descending solvent gradient from 100% petroleum ether to 80/20 pet ether/ethyl acetate as mobile phase. Elution and concentrated gave α-(methoxyimino)-N-methyl-2-[[[3-chloro-5-(t-butoxycarbonyl)-2-pyridinyl]oxy]methyl]-3-fluoro-benzeneacetamide (520 mg) as an oil. (98% E isomer; 2% Z isomer).

Example 43

α-(Methoxyimino)-N-methyl-2-[[[3-chloro-5-(t-butoxycarbonyl)-2-pyridinyl]oxy]methyl]-3-chloro-benzeneacetamide

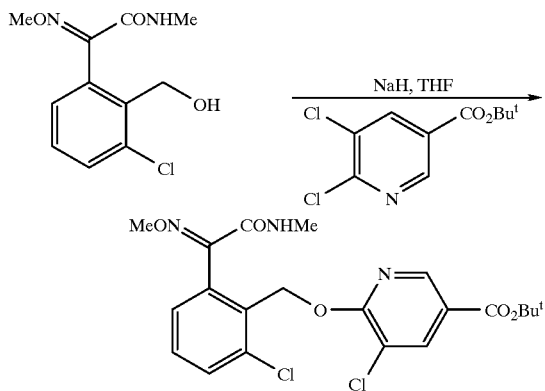

Sodium hydride (60%, 0.12 g, 3.0 mmol) was added to a solution of 3-chloro-2-hydroxymethyl-α-methyoxyimino-N-methyl-benzeneacetamide (0.43 g, 1.68 mmol) in dry THF (10 mL) and stirred for 10 minutes at 25° C. under N$_2$ atmosphere. 5,6-Dichloronicotinic acid; t-butyl ester (0.44 g, 1.87 mmol) in 2–3 mL THF was added to this reaction mixture and stirred at 25° C. for about two hours. Water (40 mL) was added and the resulting mixture was extracted with ether (2×), dried (anhydrous Na$_2$SO$_4$), filtered and concentrated in vacuo to yield 0.72 g crude oil. The oil was chromatographed with dry pack silica gel (230–400 mesh) with descending solvent gradient from 100% petroleum ether to 80/20 pet ether/ethyl acetate as mobile phase. Elution and concentration gave α-(methoxyimino)-N-methyl-2-[[[3-chloro-5-(t-butoxycarbonyl)-2-pyridinyl]oxy]methyl]-3-chloro-benzeneacetamide (430 mg) as an oil. (95% E isomer; 5% Z isomer).

Example 44

α-(Methoxyimino)-N-methyl-2-[[3-chloro-5-(t-butoxycarbonyl)-2-pyridinyl]oxy]-benzeneacetamide

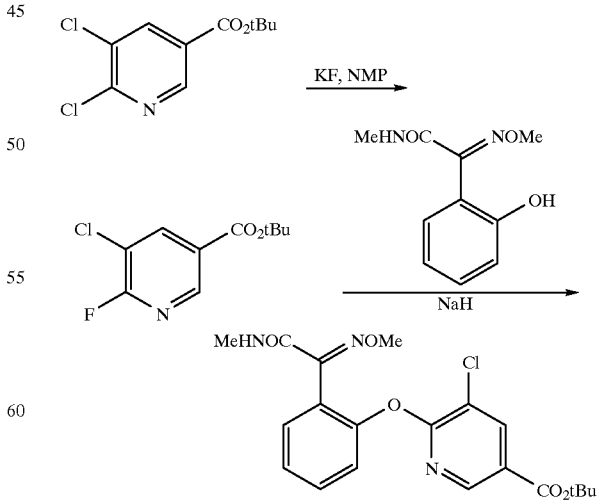

To a 100 mL flask equipped with magnetic stirrer was added 5,6-dichloronicotinic acid: t-butyl ester (5.0 g, 0.02 mol), n-methylpyrrolidinone (NMP) (5mL), diglyme (1 mL, internal standard) and spray dried KF (5.8 g, 0.1 mol). The slurry was heated to 120° C. for three hours. The mixture was cooled and partitioned between 1,1,2,2-tetrachloroethylene (30 mL) and water. The aqueous phase was extracted with 1,1,2,2,-tetrachloroethylene (30 mL) and the organic phases combined, extracted with 1N NaOH, dried ($Na_2SO_4$) and the solvent removed in vacuo to give 3.3 g of solid product that was determined to be 70% 5-chloro-6-fluoronicotinic acid: t-butyl ester and 30% 5,6-dichloronicotinic acid: t-butyl ester. This product was added to a mixture of methylene chloride (10 mL), 2-hydroxy-α-methyoxyimino-N-methyl-benzeneacetamide (0.5 g, 2.4 mmol), powdered potassium carbonate (0.82 g, 6.0 mmol) and tetra-butylammonium bromide (0.08 g, 0.25 mmol). After 24 hours, the mixture was added to ether and extracted with dilute sulfuric acid, water, and 1N NaOH. The solvent was removed in vacuo and the residue was given a chromatographic separation over silica gel using 15% acetonitrile: 85% methylene chloride to give α-(Methoxyimino)-N-methyl-2-[[3-chloro-5 -(t-butoxycarbonyl)-2-pyridinyl]oxy]-benzeneacetamide (0.169 g).

The following table identifies several compounds of formula (1), prepared analogous to the various procedures illustrated in the preceding examples, wherein X or $CO_2R$ are independently $R^1$, $R^2$, $R^3$, or $R^4$ as indicated by the following formula:

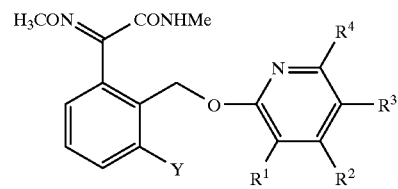

| Compound | $R^1$ | $R^2$ | $R^3$ | $R^4$ | Y |
|---|---|---|---|---|---|
| 1 | —H | —H | —$CO_2CH_2Ph$ | —F | —H |
| 2 | —$CO_2CH_2Ph$ | —H | —H | —F | —H |
| 3 | —H | —$CO_2CH_3$ | —H | —Cl | —H |
| 4 | —H | —$CO_2CH_3$ | —H | —$CO_2CH_3$ | —H |
| 5 | —H | —Cl | —$CO_2Et$ | —H | —H |
| 6 | —H | —H | —H | —$CO_2CH_3$ | —H |
| 7 | —$NO_2$ | —H | —Cl | —$CO_2CH_3$ | —H |
| 8 | —Cl | —Cl | —Cl | —$CO_2CH_3$ | —H |
| 9 | —Cl | —H | —$CO_2iPr$ | —H | —H |
| 10 | —Cl | —H | —$CO_2CH_3$ | —H | —H |
| 11 | —H | —H | —$CO_2iPr$ | —H | —H |
| 12 | —Cl | —H | —H | —$CO_2iPr$ | —H |
| 13 | —Cl | —H | —$CO_2Et$ | —H | —H |
| 14 | —Br | —H | —$CO_2Et$ | —H | —H |
| 15 | —Cl | —H | —$CO_2C_2H_4CH(CH_3)_2$ | —H | —H |
| 16 | —Cl | —H | —$CO_2nPr$ | —H | —H |
| 17 | —Cl | —H | —$CO_2tBu$ | —H | —H |
| 18 | —Cl | —H | —$CO_2CH_2iPr$ | —H | —H |
| 19 | —Cl | —H | —$CO_2$-cyclohexyl | —H | —H |
| 20 | —Cl | —H | —$CO_2iPr$ | —H | —H |
| 21 | —$CO_2CH_3$ | —H | —H | —H | —H |
| 22 | —Cl | —H | —$CO_2CH_2Ph$ | —H | —H |
| 23 | —Cl | —H | —$CO_2nBu$ | —H | —H |
| 24 | —Cl | —H | —$CO_2Ph$ | —H | —H |
| 25 | —$CO_2iPr$ | —H | —$CO_2iPr$ | —H | —H |
| 26 | —F | —H | —$CO_2iPr$ | —H | —H |
| 27 | —Br | —H | —$CO_2iPr$ | —H | —H |
| 28 | —H | —H | —Cl | —$CO_2iPr$ | —H |
| 29 | —Cl | —H | —$CO_2$-2-Et-hexyl | —H | —H |
| 30 | —$CO_2iPr$ | —H | —Cl | —H | —H |
| 31 | —Cl | —H | —$CO_2sBu$ | —H | —H |
| 32 | —Cl | —H | —$CO_2$—$C(CH_3)_2CCH$ | —H | —H |
| 33 | —Cl | —H | —H | —$CO_2tBu$ | —H |
| 34 | —$CO_2iPr$ | —H | —H | —Cl | —H |
| 35 | —$CH_3$ | —H | —$CO_2iPr$ | —H | —H |
| 36 | —Cl | —H | —$CO_2$-6-Me-2-heptyl | —H | —H |
| 37 | —$CO_2iPr$ | —H | —H | —F | —H |
| 38 | —H | —H | —$CO_2iPr$ | —F | —H |
| 39 | —H | —H | —$CO_2iPr$ | —F | —H |
| 40 | —Cl | —H | —$CO_2$-3-Me-3-pentyl | —H | —H |
| 41 | —Cl | —H | —$CO_2iPr$ | —Cl | —H |
| 42 | —$CO_2iPr$ | —H | —Cl | —Cl | —H |
| 43 | —Cl | —H | —$CO_2$—$C(CH_3)_2CHCH_2$ | —H | —H |
| 44 | —Cl | —H | —$CO_2$-2,4-di-Me-3-pentyl | —H | —H |
| 45 | —$CO_2tBu$ | —H | —H | —Cl | —H |
| 46 | —H | —H | —H | —$CO_2iPr$ | —H |
| 47 | —Cl | —H | —Cl | —$CO_2iPr$ | —H |
| 48 | —Cl | —H | —$CO_2$-2,4-di-Me-2-pentyl | —H | —H |
| 49 | —Cl | —H | —$CO_2tAmyl$ | —H | —H |
| 50 | —Cl | —H | —$CO_2$-3-Et-3-pentyl | —H | —H |

-continued

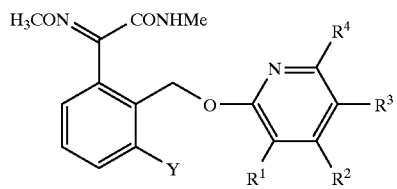

| Compound | R¹ | R² | R³ | R⁴ | Y |
|---|---|---|---|---|---|
| 51 | —CO₂-3-Me-3-pentyl | —H | —Cl | —Cl | —H |
| 52 | —CO₂tBu | —H | —Cl | —Cl | —H |
| 53 | —Cl | —H | —CO₂tBu | —Cl | —H |
| 54 | —Cl | —H | —CO₂—C(Me)₂-t-Bu | —H | —H |
| 55 | —Cl | —H | —CO₂-3-Me-3-pentyl | —Cl | —H |
| 56 | —CO₂-2,4-di-Me-3-pentyl | —H | —Cl | —Cl | —H |
| 57 | —Cl | —H | —CO₂-2,4-di-Me-3-pentyl | —Cl | —H |
| 58 | —Cl | —H | linalooyl | —H | —H |
| 59 | —CO₂-2-Et-hexyl | —H | —Cl | —Cl | —H |
| 60 | —Cl | —H | —CO₂-2-Et-hexyl | —Cl | —H |
| 61 | —Cl | —H | —CO₂—C(Me)₂-t-Bu | —Cl | —H |
| 62 | —CO₂—C(Me)₂-t-Bu | —H | —Cl | —Cl | —H |
| 63 | —Br | —H | —CO₂—C(Me)₂-t-Bu | —H | —H |
| 64 | —CF₃ | —H | —CO₂iPr | —H | —H |
| 65 | —CF₃ | —H | —CO₂tBu | —H | —H |
| 66 | —Cl | —H | —Cl | —CO₂tBu | —H |
| 67 | —Cl | —H | —H | —CO₂tAmyl | —H |
| 68 | —Cl | —H | —H | —CO₂-2,4-di-Me-3-pentyl | —H |
| 69 | —Cl | —H | —H | —CO₂-2-Et-hexyl | —H |
| 70 | —Cl | —H | —H | —CO₂—C(Me)₂-t-Bu | —H |
| 71 | —Cl | —H | —H | —CO₂-3-Et-3-pentyl | —H |
| 72 | —CF₃ | —H | —CO₂-3-Me-3-pentyl | —H | —H |
| 73 | —Br | —H | —CO₂-2,4-di-Me-3-pentyl | —H | —H |
| 74 | —Br | —H | —CO₂-3-Et-3-pentyl | —H | —H |
| 75 | —Br | —H | —CO₂-3-Me-3-pentyl | —H | —H |
| 76 | —Br | —H | —CO₂tBu | —H | —H |
| 77 | —Br | —H | —CO₂tAmyl | —H | —H |
| 78 | —F | —H | —CO₂tBu | —H | —H |
| 79 | —F | —H | —CO₂-3-Me-3-pentyl | —H | —H |
| 80 | —H | —H | —Cl | —CO₂tBu | —H |
| 81 | —Br | —H | —CO₂—C(CH₃)₂CHCH₂ | —H | —H |
| 82 | —CO₂-3-Et-3-pentyl | —H | —Cl | —Cl | —H |
| 83 | —Cl | —H | —CO₂-3-Et-3-pentyl | —Cl | —H |
| 84 | —CO₂-2-Et-hexyl | —H | —H | —Cl | —H |
| 85 | —H | —H | —CO₂-2-Et-hexyl | —Cl | —H |
| 86 | —Cl | —H | —COOH | —H | —H |
| 87 | —CO₂iPr | —H | —CH₃ | —H | —H |
| 88 | —CH₃ | —H | —CO₂tBu | —H | —H |
| 89 | —CCl3 | —H | —CO₂iPr | —H | —H |
| 90 | —CO₂tAmyl | —H | —Cl | —Cl | —H |
| 91 | —Cl | —H | —CO₂tAmyl | —Cl | —H |
| 92 | —Cl | —H | —CO₂—CH₂CF₃ | —H | —H |
| 93 | —H | —H | —H | —CO₂tBu | —H |
| 94 | —H | —H | —Cl | —CO₂-3-Me-3-pentyl | —H |
| 95 | —H | —H | fenchyl | —H | —H |
| 96 | —Cl | —H | —CO₂—CH(CF₃)₂ | —H | —H |
| 97 | —CO₂iPr | —H | —CF₃ | —H | —H |
| 98 | —Cl | —H | —CO₂—C(CH₃)₂CN | —H | —H |
| 99 | —Cl | —H | —CO₂—CH(CH₃)CH₂OMe | —H | —H |
| 100 | —Cl | —H | —CO₂—C(CH₃)₂CH₂Cl | —H | —H |
| 101 | —Cl | —H | —CO₂—C(CH₃)₂CO₂-t-Bu | —H | —H |
| 102 | —Cl | —H | —CO₂—C(CH₃)₂Ph | —H | —H |
| 103 | —Cl | —H | —CO₂—C₂H₄-TMS | —H | —H |
| 104 | —Cl | —H | 2-(4-fluorophenyl)-4,4-dimethyl-1-pentyn-3-yl | —H | —H |
| 105 | —Cl | —H | —CO₂—C₂H₄—OEt | —H | —H |
| 106 | —Cl | —H | —CO₂—CH(CH₃)C₂F₅ | —H | —H |
| 107 | —Cl | —H | 1-ethynyl-cyclopentyl | —H | —H |
| 108 | —Cl | —H | —CO₂-cyclobutyl | —H | —H |
| 109 | —Cl | —H | —H | —CO₂-3-Me-3-pentyl | —H |
| 110 | —Cl | —H | —CO₂-(1-Me-cyclopentyl) | —H | —H |
| 111 | —Cl | —H | —CO₂-(1-adamantyl) | —H | —H |
| 112 | —Cl | —H | 1,3-dimethylcyclopentyl | —H | —H |
| 113 | —Cl | —H | 2,2-dimethyl-3-(4-tolyl)-propyl | —H | —H |
| 114 | —Cl | —H | —CO₂-2-adamantyl | —H | —H |
| 115 | —Cl | —H | —CO₂—CPh₂-CO₂Et | —H | —H |
| 116 | —Cl | —H | —CO₂-3-Me-4-buten-1-yl | —H | —H |

-continued

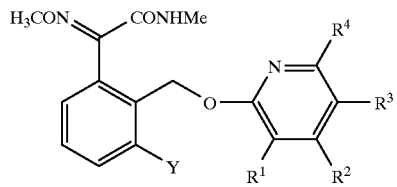

| Compound | R¹ | R² | R³ | R⁴ | Y |
|---|---|---|---|---|---|
| 117 | —Cl | —H | 4-chloro-3-methylbutyl | —H | —H |
| 118 | Cl | H | CO₂t-Bu | H | F |
| 119 | Cl | H | CO₂t-Bu | H | Cl |
| 120 | Cl | H | CO₂iso-Pr | H | F |
| 121 | Cl | H | CO₂iso-Pr | H | Cl |
| 122 | H | H | Cl | CO₂t-Bu | F |
| 123 | H | H | Cl | CO₂t-Bu | Cl |
| 124 | CH₃ | H | CO₂t-Bu | H | F |

The compounds of formula (I) thus produced are usually obtained as a mixture of the E and Z forms, which can be separated into each of those forms, if desired by chromatography.

The compounds of formula (I) show strong fungicidal activity against a wide variety of fungi. The following tests illustrate the fungicidal efficacy of the compounds invention.

Fungicide Utility

The compounds of the present invention have been found to control fungi, particularly plant pathogens. When employed in the treatment of plant fungal diseases, the compounds are applied to the plants in a disease inhibiting and phytologically acceptable amount. Application may be performed before and/or after the infection with fungi on plants. Application may also be made through treatment of seeds of plants, soil where plants grow, paddy fields for seedlings, or water for perfusion.

As used herein, the term "disease inhibiting and phytologically acceptable amount", refers to an amount of a compound of the present invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 lb/A.

The compounds of the invention may also be used to protect stored grain and other non-plant loci from fungal infestation.

The following experiments were performed in the laboratory to determine the fungicidal efficacy of the compounds of the invention.

Compound Formulation: Compound formulation was accomplished by dissolving technical materials in acetone, with serial dilutions then made in acetone to obtain desired rates. Final treatment volumes were obtained by adding nine volumes 0.05% aqueous Tween-20 or Triton X-100, depending upon the pathogen.

Powdery Mildew of Wheat (*Erysiphe graminis*-ERYSGT): Wheat (cultivar Monon) was grown in a soilless peat-based potting mixture ("Metromix") until the seedlings were 10–20 cm tall. These plants were then inoculated with *Erysiphe graminis* by dusting spores from stock plants onto the test plants. After 48 hours the plants were sprayed to run off with the test compound at a rate of 25 ppm and then kept in the greenhouse until disease developed on the untreated control plants.

Leaf blotch of Wheat (*Septoria tritici*-SEPTTR): Wheat (cultivar Monon) was grown in a soilless peat-based potting mixture ("Metromix") until the seedlings were 10–20 cm tall. These plants were then sprayed to run off with the test compound at a rate of 25 ppm. After 24 hours the test plants were inoculated by spraying with an aqueous spore suspension of *Septoria tritici*. The plants were then transferred to the greenhouse until disease developed on the untreated control plants.

Downy Mildew of Grape (*Plasmopara viticola*-PLASVI) (24 Hour Protectant): Vines (cultivar Carignane) were grown from seed in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous sporangia suspension of *Plasmopara viticola*. The plants were then transferred to the greenhouse until disease developed on the untreated control plants.

Downy Mildew of Grape (*Plasmopara viticola*-PLASVI) (96 Hour Protectant): Vines (cultivar Carignane) were grown from seed in a soilless peat-based potting mixture ("Metromix") until the seedlings were 10–20 cm tall. These plants were then sprayed to run off with the test compound at a rate of 100 ppm. After 96 hours the test plants were inoculated by spraying with an aqueous sporangia suspension of *Plasmopara viticola*. The plants were then transferred to the greenhouse until disease developed on the untreated control plants.

Powdery Mildew of Grape (*Uncinula necator*-UNCINE): Vines (cultivar Carignane) were grown from seed in a soilless peat-based potting mixture ("Metromix") until the seedlings were 10–20 cm tall. These plants were then sprayed to run off with the test compound at a rate of 100 ppm. After 168 hours the test plants were inoculated with *Uncinula necator* by dusting spores from stock plants onto the test plants. The plants were then transferred to the greenhouse until disease developed on the untreated control plants.

Apple Scab (*Venturia inaequalis*-VENTIN): Apples (cultivar Red Delicious) were grown from seed in a soilless peat-based potting mixture ("Metromix") until the seedlings were 10–20 cm tall. These plants were then sprayed to run off with the test compound at a rate of 100 ppm. After 48 hours the test plants were inoculated by spraying with an aqueous suspension of *Venturia inaequalis* spores. The plants were then transferred to the greenhouse until disease developed on the untreated control plants.

Rice Blast (*Pyricularia oryzae*-PYRIOR): Rice (cultivar M9) was grown from seed in a soilless peat-based potting mixture ("Metromix") until the seedlings were 10–20 cm tall. These plants were then sprayed to run off with the test compound at a rate of 25 ppm. After 96 hours the test plants were inoculated by spraying with an aqueous suspension of *Pyricularia oryzae conidia*. The plants were then transferred to the greenhouse until disease developed on the untreated control plants.

Rice Sheath Blight (*Rhizoctonia solani*-RHIZSO): Rice (cultivar M9) was grown from seed in a soilless peat-based potting mixture ("Metromix") until the seedlings were 10–20 cm tall. These plants were then sprayed to run off with the test compound at a rate of 25 ppm. After 24 hours the test plants were inoculated using *Rhizoctonia solani* infested barley seed. The plants were then transferred to the greenhouse until disease developed on the untreated control plants.

The following table presents the activity of typical compounds of the present invention when evaluated in these experiments. The effectiveness of the test compounds in controlling disease was rated using the following scale:

blank space=not tested
−=0–24% control of plant disease
+=25–74% control of plant disease
++=75–100% control of plant disease

| Compound number | PLASVI (24 HR) | PLASVI (96 HR) | VENTIN | UNCINE | PYRIOR | RHIZSO | ERYSGT | SEPTTR |
|---|---|---|---|---|---|---|---|---|
| 1 | − | | − | − | − | − | − | − |
| 2 | ++ | | ++ | − | − | − | + | + |
| 3 | + | | − | − | − | − | | |
| 4 | + | | − | − | − | − | − | + |
| 5 | ++ | | ++ | ++ | − | − | + | − |
| 6 | + | | − | − | − | − | + | + |
| 7 | ++ | | ++ | − | − | − | ++ | + |
| 8 | + | | − | + | − | − | + | − |
| 9 | ++ | | ++ | ++ | ++ | ++ | ++ | + |
| 10 | ++ | | − | ++ | − | − | ++ | + |
| 11 | ++ | | ++ | ++ | − | + | ++ | ++ |
| 12 | ++ | | ++ | ++ | ++ | ++ | ++ | ++ |
| 13 | ++ | | + | ++ | + | − | ++ | + |
| 14 | ++ | | ++ | ++ | + | + | ++ | + |
| 15 | ++ | | ++ | ++ | + | + | ++ | + |
| 16 | ++ | | ++ | ++ | ++ | + | ++ | + |
| 17 | ++ | | ++ | ++ | ++ | ++ | ++ | ++ |
| 18 | ++ | | ++ | ++ | ++ | + | ++ | ++ |
| 19 | ++ | | ++ | ++ | + | + | ++ | ++ |
| 20 | | | | | | | ++ | ++ |
| 21 | − | | − | − | | | − | + |
| 22 | ++ | | ++ | ++ | | | ++ | ++ |
| 23 | | | ++ | ++ | | | ++ | + |
| 24 | + | | − | − | | | − | + |
| 25 | + | | − | − | | | − | + |
| 26 | ++ | | ++ | ++ | | | ++ | ++ |
| 27 | ++ | | ++ | ++ | | | ++ | ++ |
| 28 | ++ | | ++ | ++ | | | ++ | ++ |
| 29 | ++ | | ++ | ++ | | | ++ | ++ |
| 30 | − | | ++ | + | | | − | − |
| 31 | ++ | | ++ | ++ | | | ++ | ++ |
| 32 | ++ | | ++ | ++ | | | ++ | ++ |
| 33 | ++ | | + | ++ | | | ++ | + |
| 34 | + | | + | + | | | + | − |
| 35 | ++ | | ++ | ++ | | ++ | ++ | |
| 36 | ++ | | ++ | ++ | | | ++ | ++ |
| 37 | ++ | | ++ | ++ | | | ++ | + |
| 38 | | | ++ | + | | | + | + |
| 39 | ++ | | ++ | ++ | | | ++ | ++ |
| 40 | ++ | | ++ | ++ | | | ++ | ++ |
| 41 | ++ | | ++ | ++ | | | ++ | ++ |
| 42 | + | | ++ | ++ | | | + | + |
| 43 | ++ | | ++ | ++ | | | ++ | ++ |
| 44 | | ++ | ++ | ++ | | | ++ | ++ |
| 45 | − | | − | + | | | − | ++ |
| 46 | | + | ++ | ++ | | | ++ | + |
| 47 | | ++ | ++ | ++ | | | ++ | ++ |
| 48 | | ++ | | | | | ++ | ++ |
| 49 | | ++ | ++ | ++ | | | ++ | ++ |
| 50 | | ++ | ++ | ++ | | | ++ | ++ |
| 51 | | − | − | + | | | + | + |
| 52 | | ++ | ++ | ++ | | | + | + |
| 53 | | ++ | ++ | ++ | | | ++ | ++ |

-continued

| Compound number | PLASVI (24 HR) | PLASVI (96 HR) | VENTIN | UNCINE | PYRIOR | RHIZSO | ERYSGT | SEPTTR |
|---|---|---|---|---|---|---|---|---|
| 54 |  | ++ | ++ | ++ |  |  | ++ | ++ |
| 55 |  | ++ | ++ | ++ |  |  | ++ | ++ |
| 56 |  | − | + | − |  |  | − | + |
| 57 |  | ++ |  |  |  |  | ++ | ++ |
| 58 |  | ++ | ++ | ++ |  |  | + | − |
| 59 |  | − |  |  |  |  | − | + |
| 60 |  | ++ |  |  |  |  | ++ | ++ |
| 61 |  | ++ |  |  |  |  | ++ | ++ |
| 62 |  |  |  |  |  |  | − | − |
| 63 |  | ++ | ++ | ++ |  |  | ++ | ++ |
| 64 |  | ++ | ++ | ++ |  |  | ++ | ++ |
| 65 |  | ++ |  |  |  |  | ++ | ++ |
| 66 |  | ++ | ++ | ++ |  |  | ++ | ++ |
| 67 |  | + |  |  |  |  | + | − |
| 68 |  | ++ |  |  |  |  | ++ | + |
| 69 |  | + |  |  |  |  | + | ++ |
| 70 |  | ++ |  |  |  |  | + | + |
| 71 |  | ++ |  |  |  |  | + | + |
| 72 |  | ++ |  |  |  |  | ++ | ++ |
| 73 |  | ++ | ++ | ++ |  |  | ++ | ++ |
| 74 |  | ++ | ++ | ++ |  |  | ++ | ++ |
| 75 |  | ++ | ++ | ++ |  |  | ++ | ++ |
| 76 |  | ++ | ++ | ++ |  |  | ++ | ++ |
| 77 |  | ++ |  |  |  |  | ++ | ++ |
| 78 |  | ++ |  |  |  |  | ++ | ++ |
| 79 |  | ++ |  |  |  |  | ++ | ++ |
| 80 |  | ++ |  |  |  |  | ++ | ++ |
| 81 |  | ++ |  |  |  |  | ++ | ++ |
| 82 |  | − |  |  |  |  | − | + |
| 83 |  | ++ |  |  |  |  | ++ | ++ |
| 84 |  | + |  |  |  |  | + | + |
| 85 |  | ++ |  |  |  |  | ++ | ++ |
| 86 |  | − |  |  |  |  | − | + |
| 87 |  | ++ |  |  |  |  |  |  |
| 88 |  | ++ |  |  |  |  |  |  |
| 89 |  |  |  |  |  |  |  |  |
| 90 |  | ++ |  |  |  |  |  |  |
| 91 |  | ++ |  |  |  |  |  |  |
| 92 |  | ++ |  |  |  |  |  |  |
| 93 |  | ++ |  |  |  |  |  |  |
| 94 |  | ++ |  |  |  |  |  |  |
| 95 |  | ++ |  |  |  |  |  |  |
| 96 |  | ++ |  |  |  |  |  |  |
| 97 |  | + |  |  |  |  |  |  |
| 98 |  | ++ |  |  |  |  |  |  |
| 99 |  | ++ |  |  |  |  |  |  |
| 100 |  | ++ |  |  |  |  |  |  |
| 101 |  | ++ |  |  |  |  |  |  |
| 102 |  | ++ |  |  |  |  |  |  |
| 103 |  | ++ |  |  |  |  |  |  |
| 104 |  | ++ |  |  |  |  |  |  |
| 105 |  | ++ |  |  |  |  |  |  |
| 106 |  | ++ |  |  |  |  |  |  |
| 107 |  | ++ |  |  |  |  |  |  |
| 108 |  | ++ |  |  |  |  |  |  |
| 109 |  | ++ |  |  |  |  |  |  |
| 110 |  | ++ |  |  |  |  |  |  |
| 111 |  | ++ |  |  |  |  |  |  |
| 112 |  |  |  |  |  |  |  |  |
| 113 |  | ++ |  |  |  |  |  |  |
| 114 |  | ++ |  |  |  |  |  |  |
| 115 |  |  |  |  |  |  |  |  |
| 116 |  |  |  |  |  |  |  |  |
| 117 |  |  |  |  |  |  |  |  |
| 118 |  |  |  |  |  |  |  |  |
| 119 |  |  |  |  |  |  |  |  |
| 120 |  |  |  |  |  |  |  |  |
| 121 |  |  |  |  |  |  |  |  |
| 122 |  |  |  |  |  |  |  |  |
| 123 |  |  |  |  |  |  |  |  |
| 124 |  |  |  |  |  |  |  |  |
| 125 |  |  |  |  |  |  |  |  |

The compounds of formula (I) may be applied directly, or more preferably applied in the form of a composition, which are important embodiments of the invention, and which comprise one or more compounds of formula (1) with a phytologically-acceptable inert carrier. The composition may optionally include fungicidal combinations which comprise at least 1% of one or more compounds of formula (1) with another fungicide, herbicide, and/or insecticide.

The compositions are either concentrated formulations which are dispersed in water for application, or are dust or granular formulations which are applied without further treatment. The compositions are prepared according to procedures which are conventional in the agricultural chemical art, but which are novel and important because of the presence therein of the compounds of this invention. Some description of the formulation of the compositions will, however, be given to assure that agricultural chemists can readily prepare any desired composition.

The dispersions in which the compounds are applied are most often aqueous suspensions or emulsions prepared from concentrated formulations of the compounds. Such water-soluble, water suspendable, or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to 90%. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the naphthalenesulfonates, alkylbenzenesulfonates, the alkyl sulfates, and non-ionic surfactants, such as, for example, ethylene oxide adducts of alkyl phenols.

Emulsifiable concentrates of the compounds comprise a convenient concentration of a compound, such as from about 10% to about 50% of liquid, dissolved in an inert carrier, which is either a water miscible solvent or a mixture of water-immiscible organic solvents, and emulsifiers. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol. Suitable emulsifiers for emulsifiable concentrates are chosen from conventional nonionic surfactants, such as those mentioned above.

Aqueous suspensions comprise suspensions of water-insoluble compounds of this invention, dispersed in an aqueous vehicle at a concentration in the range from about 5% to about 50%. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% of the compound, dispersed in an inert carrier which consists entirely of in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle.

Dusts containing the compounds are prepared simply by intimately mixing the compound in powdered form with a suitable dusty agricultural carrier, such as, for example, kaolin clay, ground volcanic rock, and the like. Dusts can suitably contain from about 1% to about 10% of the compound.

What is claimed is:

1. A compound of Formula (1)

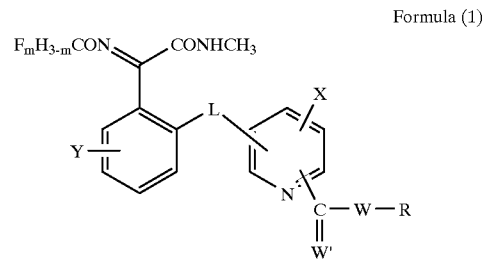

Formula (1)

wherein m is an integer 0–3;

Y is H, halogen, $C_{1-4}$ alkyl, $C_{1-4}$ alkoxy, or $C_{1-4}$ alkylthio;

X is H, $C_{1-6}$alkyl, $C_{1-6}$alkoxy, halo-$C_{1-6}$alkyl, halo-$C_{1-6}$ alkoxy, halo, nitro, carbo-$C_{1-6}$alkoxy, cyano, $C_{1-6}$alkylthio, or halo-$C_{1-6}$alkylthio;

W or W' is independently O or S;

R is H, $C_{1-6}$alkyl, or $C_{3-7}$cycloalkyl; optionally substituted by halo-$C_{1-6}$alkyl, halo-$C_{1-6}$alkoxy, $C_{2-6}$alkenyl, halo-$C_{2-6}$alkenyl, $C_{2-6}$alkynyl, —C≡N, $C_{1-6}$ alkoxy, halogen, aryl, substituted aryl, or Pyridyl; and L is —O—, —$CH_2$—, —$SO_n$—, —$CH_2O$—, —$OCH_2$—, —$CH_2S$—, —$SCH_2$—, —CH═CH—, —C≡C—, or

, wherein n is an integer 0–2.

2. A compound of claim 1 of the formula

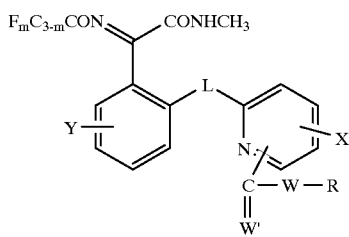

wherein the substituents are as defined in claim 1.

3. A compound of claim 2 of the formula

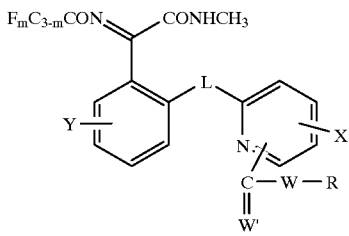

wherein Y is halogen and the remaining substituents are as defined in claim 2.

4. A compound of claim 3 of the formula

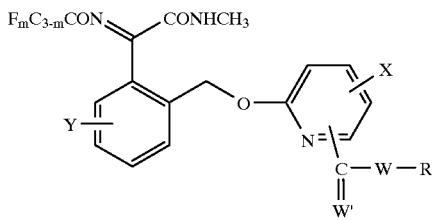

wherein Y is halogen and the remaining substituents are as defined in claim 3.

5. A compound of claim 4 of the formula

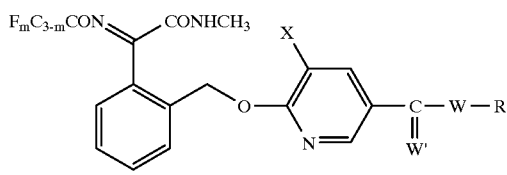

wherein the substituents are as defined in claim 4.

6. A compound of claim 5 wherein X is $C_{1-4}$ alkyl, halo, or halo-$C_{1-4}$ alkyl, and R is C1-4 alkyl, optionally substituted by alkenyl, alkynyl, or alkoxy.

7. A compound of claim 5 wherein X is chloro, m is 0, W is O, W' is O, and R is isopropyl.

8. A compound of claim 5 wherein X is chloro, m is 0, W is O, W' is O, and R is t-butyl.

9. A compound of claim 5 wherein X is methyl, m is 0, W is O, W' is O, and R is isopropyl.

10. A compound of claim 5 wherein X is methyl, m is 0, W is O, W' is O, and R is t-butyl.

11. A compound of claim 5 wherein X is trifluoromethyl, m is 0, W is O, W' is O, and R is t-butyl.

12. A compound of claim 5 wherein X is chloro, m is 0, W is O, W' is O, and R is t-amyl.

13. A compound of claim 4 of the formula

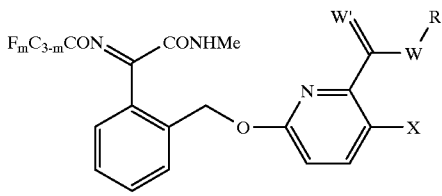

wherein the substituents are as defined in claim 4.

14. A compound of claim 13 wherein X is chloro, m is 0, W is O, W' is O, and R is t-butyl.

15. A process for preparing a compound of formula (a)

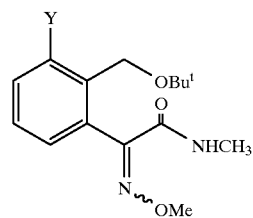

wherein Y is chloro or fluoro;

which comprises:
reacting a compound of the formula (b)

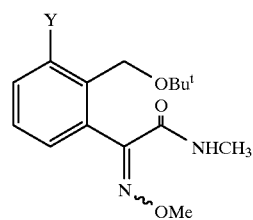

with p-toluenesulfonic acid to give the compound of formula (a).

16. A fungicidal method which comprises applying to the locus to be treated a fungicidally-effective amount of a compound of formula (1)

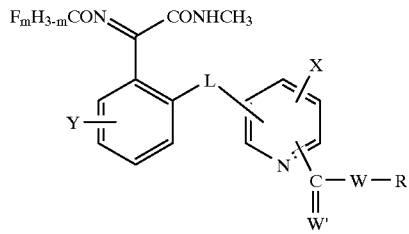

Formula (1)

wherein
m is an integer 0–3;
Y is H, halogen, $C_{1-4}$ alkyl, $C_{1-4}$ alkoxy, $C_{1-4}$ alkylthio;
X is H, $C_{1-6}$alkyl, $C_{1-6}$alkoxy, halo-$C_{1-6}$alkyl, halo-$C_{1-6}$alkoxy, halo, nitro, carbo-$C_{1-6}$alkoxy, cyano, $C_{1-6}$alkylthio, or halo-$C_{1-6}$alkylthio;
W or W' is independently O or S;
R is H, $C_{1-6}$alkyl, or $C_{3-7}$cycloalkyl; optionally substituted by halo-$C_{1-6}$alkyl, halo-$C_{1-6}$alkoxy, $C_{2-6}$alkenyl, halo-$C_{2-6}$alkenyl, $C_{2-6}$alkynyl, —C≡N, $C_{1-6}$ alkoxy, halogen, aryl, substituted aryl, or pyridyl; and
L is —O—, —CH$_2$—, —SO$_n$—, —CH$_2$O—, —OCH$_2$—, —CH$_2$S—, —SCH$_2$—, —CH=CH—, —C≡C—, or

, wherein n is an integer 0–2.

UNITED STATES PATENT AND TRADEMARK OFFICE
CERTIFICATE OF CORRECTION

PATENT NO. : 5,968,875
DATED : October 19, 1999
INVENTOR(S) : Scott J. Bis, et al.

It is certified that error appears in the above-identified patent and that said Letters Patent is hereby corrected as shown below:

In claim 15 (Col. 42) in formula (b), delete "NHCH$_3$" and insert ---OEt--- therefore.

Signed and Sealed this

Thirteenth Day of June, 2000

Attest:

Q. TODD DICKINSON

*Attesting Officer*         *Director of Patents and Trademarks*

UNITED STATES PATENT AND TRADEMARK OFFICE
CERTIFICATE OF CORRECTION

PATENT NO. : 5,968,875
DATED : October 19, 1999
INVENTOR(S) : Scott J. Bis, Emily J. Canada, David H. Cooper, Christopher S. Galka, Neil Kirby, David G. Ouimette, David E. Podhorez, Mary Pieczko, Rebecca Rezac, Brent J. Rieder John K. Swayze, Vidyadhar B. Hedge, Gary L. Sampson It is certified that error appears in the above-identified patent and that said Letters Patent is hereby corrected as shown below:

Column 2,
Formula (2), that portion of the formula reading "$C_{3-m}$" should read --$H_{3-m}$--.
Formula (3), that portion of the formula reading "$C_{3-m}$" should read --$H_{3-m}$--.

Column 3,
Formula (4), that portion of the formula reading "$C_{3-m}$" should read --$H_{3-m}$--.

Claim 2, that portion of the formula reading "$C_{3-m}$" should read --$H_{3-m}$--.

Claim 3, that portion of the formula reading "$C_{3-m}$" should read --$H_{3-m}$--.

Claim 4, that portion of the formula reading "$C_{3-m}$" should read --$H_{3-m}$--.

Claim 5, that portion of the formula reading "$C_{3-m}$" should read --$H_{3-m}$--.

Claim 13, that portion of the formula reading "$C_{3-m}$" should read --$H_{3-m}$--.

Signed and Sealed this

Seventh Day of August, 2001

*Attest:*

*Attesting Officer*

NICHOLAS P. GODICI
*Acting Director of the United States Patent and Trademark Office*